(12) United States Patent
Reynolds et al.

(10) Patent No.: US 9,610,249 B2
(45) Date of Patent: Apr. 4, 2017

(54) DOSAGE AND ADMINISTRATION FOR PREVENTING CARDIOTOXICITY IN TREATMENT WITH ERBB2-TARGETED IMMUNOLIPOSOMES COMPRISING ANTHRACYCLINE CHEMOTHERAPEUTIC AGENTS

(71) Applicant: MERRIMACK PHARMACEUTICALS, INC., Cambridge, MA (US)

(72) Inventors: Joseph G. Reynolds, North Andover, MA (US); Kenneth J. Olivier, Jr., Attleboro, MA (US); Bart S. Hendriks, Belmont, MA (US); Thomas Wickham, Groton, MA (US); Stephan Klinz, Norwood, MA (US); Elena Geretti, Cambridge, MA (US)

(73) Assignee: Merrimack Pharmaceuticals. Inc., Cambridge, MA (US)

( * ) Notice: Subject to any disclaimer, the term of this patent is extended or adjusted under 35 U.S.C. 154(b) by 0 days.

(21) Appl. No.: 14/832,103

(22) Filed: Aug. 21, 2015

(65) Prior Publication Data
US 2016/0038417 A1 Feb. 11, 2016

Related U.S. Application Data

(63) Continuation of application No. 13/912,167, filed on Jun. 6, 2013, now Pat. No. 9,226,966, which is a continuation of application No. PCT/US2011/063623, filed on Dec. 6, 2011.

(60) Provisional application No. 61/449,602, filed on Mar. 4, 2011, provisional application No. 61/420,688, filed on Dec. 7, 2010, provisional application No. 61/420,225, filed on Dec. 6, 2010.

(51) Int. Cl.

| | |
|---|---|
| *A61K 9/127* | (2006.01) |
| *A61K 31/7042* | (2006.01) |
| *A61K 47/48* | (2006.01) |
| *A61K 31/704* | (2006.01) |
| *A61K 47/42* | (2017.01) |
| *G01N 33/566* | (2006.01) |
| *A61K 9/00* | (2006.01) |

(52) U.S. Cl.
CPC ............ *A61K 9/127* (2013.01); *A61K 9/0019* (2013.01); *A61K 31/704* (2013.01); *A61K 31/7042* (2013.01); *A61K 47/42* (2013.01); *A61K 47/48569* (2013.01); *A61K 47/48823* (2013.01); *G01N 33/566* (2013.01)

(58) Field of Classification Search
None
See application file for complete search history.

(56) References Cited

U.S. PATENT DOCUMENTS

| | | | |
|---|---|---|---|
| 5,593,622 A | 1/1997 | Yoshioka et al. | |
| 5,676,971 A | 10/1997 | Yoshioka et al. | |
| 5,846,458 A | 12/1998 | Yoshioka et al. | |
| 6,210,707 B1 | 4/2001 | Papahadjopoulos et al. | |
| 6,214,388 B1 | 4/2001 | Benz et al. | |
| 7,022,336 B2 | 4/2006 | Papahadjopoulos et al. | |
| 7,135,177 B2 | 11/2006 | Benz et al. | |
| 7,244,826 B1 | 7/2007 | Marks et al. | |
| 7,449,184 B2 | 11/2008 | Allison et al. | |
| 7,507,407 B2 | 3/2009 | Benz et al. | |
| 7,846,440 B2 | 12/2010 | Schoeberl et al. | |
| 7,871,620 B2 | 1/2011 | Benz et al. | |
| 7,892,554 B2 | 2/2011 | Marks et al. | |
| 2005/0084524 A1 | 4/2005 | Martin et al. | |
| 2005/0276822 A1 | 12/2005 | Wiseman et al. | |
| 2006/0258656 A1* | 11/2006 | Matteucci ............ | A61K 31/415 514/235.5 |
| 2006/0269542 A1 | 11/2006 | Hjortsvang et al. | |
| 2007/0082856 A1* | 4/2007 | Gianni ................. | A61K 31/495 514/34 |
| 2008/0108135 A1 | 5/2008 | Marks et al. | |
| 2010/0068255 A1 | 3/2010 | Benz et al. | |
| 2010/0239652 A1 | 9/2010 | Rochlitz et al. | |
| 2011/0059076 A1 | 3/2011 | Mc Donagh et al. | |

FOREIGN PATENT DOCUMENTS

| | | |
|---|---|---|
| WO | WO9738731 A1 | 10/1997 |
| WO | WO 2006116107 A2 | 11/2006 |
| WO | WO 2009126920 A2 | 10/2009 |
| WO | WO 2010059315 A1 | 5/2010 |

OTHER PUBLICATIONS

Nellis et al. (Biotechnol. Prog., 21: 205-220, 2005).*
Park et al. (Clin Cancer Res, 8: 1172-1181, 2002).*
Nellis et al. (Biotechnol. Prog., 21: 221-232, 2005).*
Exhibit A (Equivalent Surface Area Dosage Conversion Factors, 2015).*
Lazar et al. (PNAS, 103(11): 4005-4010, 2006).*
Park, J. W., et al. "Tumor targeting using anti-her2 immunoliposomes" Journal of Controlled Release, vol. 74 (2001) pp. 95-113.

(Continued)

*Primary Examiner* — Brad Duffy
*Assistant Examiner* — Nelson B Moseley, II
(74) *Attorney, Agent, or Firm* — Honigman Miller Schwartz and Cohn LLP; Fernando Alberdi; Cynthia M. Bott

(57) ABSTRACT

Methods for determining dosage of HER2-targeted anthracycline-containing immunoliposomes are disclosed, as are methods of treating cancer patients with HER2-positive tumors using dosages so determined. Upon administration, the dosages share the low cardiotoxicity profile of standard dosages of non-immunoliposomal (untargeted), anthracycline-containing liposomes.

22 Claims, 25 Drawing Sheets

(56) References Cited

OTHER PUBLICATIONS

Kirpotin, Dmitri B., et al. "Antibody Targeting of Long-Circulating Lipidic Nanoparticles Does Not Increase Tumor Localization but Does Increase Internalization in Animal Models", Cancer Res, vol. 66 (2006), pp. 6732-6740.

Corresponding Chinese Patent Application No. 201180066002.5—English Translation of Notification of the Second Office Action and Search Report, dated May 11, 2015.

Doxil® Prescribing Information, Ortho Biotech Products, LP, Raritan, NJ, May 2007.

Wickham, T.J., et al., "Preclinical safety and activity of MM-302, a HER2-targeted liposomal doxorubicin designed to have an improved safety and efficacy profile over approved anthracyclines", San Antonio Breast Cancer Symposium, Poster Presentation, 1 page, P3-14-09, Dec. 8, 2010.

Hysing, Jan, et al., "Cardiotoxic effects of trastuzumab ", Tidsskr Nor Legeforen, Nov. 15, 2011;131(22), pp. 2239-2241.

Sawyer, Douglas B., et al. "Mechanisms of Anthracycline Cardiac Injury: Can we identify strategies for cardio-protection?".

Ewer, Michael S., et al. "Cardiac Safety of Liposomal Anthracyclines," Elsevier, Seminars in Oncology (2004), pp. 161-181.

Bauwens, Celine L., et al., "Geometric Control of Cardiomyogenic Induction in Human Pluripotent Stem Cells" Tissue Eng Part A. Aug. 2011, vol. 17, No. 15-16:1901-1909 PMID 21417693.

Clinical Trials Archive: "A Phase 1, Multi-Center, Open-Label, Dose-Escalation, Safety, and Pharmacokinetic Clinical Study of Intravenously Administered MM-302 Monotherapy and in Combination with Trastuzumab with or without Cyclophosphamide in Patients with Advanced HER2 Positive Breast Cancer" Nov. 17, 2011, pp. 1-3, XP055273289, Retrieved from the Internet: URL:https://clinicaltrials.gov/archive/NCT01304797/2011_11_17 *the whole document*.

Cortes, Javier, Nonpegylated Liposomal Doxorubicin (TLC-D99), Paclitaxel, and Trastuzumab in HER-2-Overexpressing Breast Cancer. A Multicenter Phase I/II Study, Clin Cancer Res 2009;15(1), 2009, pp. 307-314 and Correction p. 1843 and cover page.

Extended European Search Report with Supplementary European Search Report, and European Search Opinion for EP 13 86 0427, issued May 30, 2016.

Fuchs, Ilka B., et al. Analysis of HER2 and HER4 in Human Myocardium to Clarify the Cardiotoxicity of Trastuzumab (HerceptinTM), Breast Cancer Res Treat. 2003;82:23-28.

Geretti, Elena, et al. "HER2-targeted liposomal doxorubicin, MM-302, has a favorable cardiosafety profile in preclinical models", American Association for Cancer Research (AACR) NCI-EORTC International Conference on Molecular Targets and Cancer Therapeutics, Nov. 12-16, 2011. (Poster #C90). Retrieved from the Internet: URL:http://www.merrimack.com/files/MM-302/Preclinical%20Posters/AACR-EORTC%202011/AACR%20Mol%20Targets%202011%20MM-302%20EG%20final.pdf.

Hendriks, Bart, et al. "Physiologically-based PK modeling of liposomal drug delivery points to a key role of tumor deposition in determining the relative efficacy of liposomal vs. free doxorubicin in breast cancer and Kaposi sarcoma", 102nd American Association for Cancer Research (AACR) Annual Meeting 2011, Apr. 2-6, 2011. Retrieved from the internet: URL: http://cancerres.aacrjournals.org/content/71/8_Supplement/4915.abstract.

Klinz, Stephan, et al. "MM-302, a HER2-targeted liposomal doxorubicin, shows binding/uptake and efficacy in HER2 2+ cells and xenograft models", 102nd American Association for Cancer Research (AACR) Annual Meeting 2011, Apr. 2-6, 2011 (Poster #3637). Retrieved from the internet: URL:http://www.merrimack.com/files/MM-302/Preclinical%20Posters/AACR%202011/10.%20AACR%202011%20MM-302%2-HER2%20Threshold%20Klintz.pdf.

Kobrinsky, Boris, et al. "Documentation of Complete Response in Metastatic Breast Cancer to Liver and Bone Achieved with Trastuzumab and Pegylated Liposomal Doxorubicin," Clinical Medicine: Oncology 2008: 2 pp. 469-470.

Mamot, Christoph, et al. "Liposome-based approaches to overcome anticancer drug resistance", Drug Resistance Updates 6 (2003), pp. 271-279.

Martin, M., et al. "Pegylated liposomal doxorubicin in combination with cyclophosphamide and trastuzumab in HER2-positive metastatic breast cancer patients: efficacy and cardiac safety from the GEICAM/2004/05 study", Annals of Oncology., vol. 22, No. 12, Mar. 17, 2011, pp. 2591-2596.

Noble, Charles O., et al. Characterization of Highly Stable Liposomal and Immunolipsomal Formulations of Vincristine and Vinblastine, Cancer Chemother. Pharmacol. 2009 64:741-751.

Wolff, Antonio, et al. "Phase II trial of pegylated liposomal doxorubicin plus docetaxel with and without trastuzumab in metastatic breast cancer: trastuzumab in metastatic breast cancer: Eastern Cooperative Oncology Group Trial E3198", Breast Cancer Research and Treatment, Kluwer Academic Publishers, BO, vol. 121, No. 1, Mar. 24, 2010, pp. 111-120.

Reynolds, Joe, et al. "MM-302, HER2-targeted liposomal doxorubicin, does not impair cardiomyocyte function in vitro", 102nd American Association for Cancer Research (AACR) Annual Meeting 2011, Apr. 2-6, 2011 (Poster #3638). Retrieved from the Internet: URL: http://www.merrimack.com/files/MM-302/Preclinical%20Posters/AACR%202011/AACR2011%20MM-302%20Cardiomyocyte%20JReynolds.pdf.

Shmeeda, H., et al. "Her2-targeted pegylated 1-15 liposomal doxorubicin: Retention of target-specific binding and cytotoxicity after in vivo passage", Journal of Controlled Release, Elsevier, Amsterdam, NL, vol. 136, No. 2, Jun. 5, 2009, pp. 155-160, XP026108534, ISSN: 0168-3659, DOI: 10.1016/J.JCONREL.2009.02.002 [retrieved on Feb. 7, 2009] *paragraph [discussion]*.

Stickeler, Elmar, et al. "Pegylated liposomal doxorubicin and trastuzumab as 1st and 2nd line therapy in her2/neu positive metastatic breast cancer: a multicenter phase II trial", Breast Cancer Research and Treatment, Kluwer Academic Publishers, BO, vol. 117, No. 3, Jan. 21, 2009, pp. 591-598.

Neve, Richard M., et al. "Biological Effects of Anti-ErbB2 Single Chain Antibodies Selected for Internalizing Function", Biochemical and Biophysical Research Communications, 280 (2001), pp. 274-279.

Nielsen, Ulrik B., et al. "Therapeutic efficacy of anti-ErbB2 immunoliposomes targeted by a phage antibody selected for cellular endocytosis" , Biochemica et Biophysica Acta, 1591 (2002), pp. 109-118.

Gianni, Luca, et al. Anthracycline Cardiotoxicity in breast cancer patients: synergism with trastuzumab and taxanes, Cardiovasc Toxicol (2007) 7:67-71.

"Assessing Surrogates of Clinical Cardiotoxicity Using Stem Cell-Derived Cardiiomyocytes" presented at Pharma/Bio Forum on Preclinical Development—Utilize Biomarkers and Leverage Partnerships for Earlier Toxicity Detection Conference, Sep. 26-27, 2011, Boston, Massachusetts (31 pages).

EPAR Summary for Caelyx, European Medicines Agency (2010) and Annex I—Summary of Product Characteristics, 46 pages.

EPAR Summary for Myocet, European Medicines Agency (2013) and Annex I—Summary of Product Characteristics, 37 pages.

Harrington, Kevin J., et al. "Effective Targeting of Solid Tumors in Patients with Locally Advanced Cancers by Radiolabeled Pegylated Liposomes", Clinical Cancer Research, vol. 7, pp. 243-254 (2001).

Mufamadi, Maluta, S., et al. "A Review on Composite Liposomal Technologies for Specialized Drug Delivery", Journal of Drug Delivery, vol. 2011, Article ID 939851, 19 pages.

O'Brien, M.E.R., et al. Reduced cardiotoxicity and comparable efficacy in a phase III trial of pegylated liposomal doxorubicin HCI (CAELYXTM/Doxil®) versus conventional doxorubicin for first-line treatment of metastatic breast cancer, Annals of Oncology 15:440-449 (2004).

Siwak, D., et al. Commentary re: J. W. Park et al., The potential of drug-carrying immunoliposomes as anticancer agents, Clinical Cancer Research 8 (2002) pp. 955-956.

Doxorubicin Hydrochloride for Injection, USP Packaging Label, Pfizer, Inc., Revised May 2010, pp. 1-22.

Reynolds, J., et al. "MM-302, a Her2-Targeted Liposomal Doxorubicin, Limits Doxorubicin Accumulation in

(56) References Cited

OTHER PUBLICATIONS

Cardiomyocytes, and Enhances Doxorubicin Uptake into Tumor Cells in Vitro" Society of Toxicology, 50th Annual Meeting and ToxExpo, Washington, D.C., ISSN: 1096-6080, vol. 120, Suppl. 2, Mar. 6-10, 2011 (Abstract 1888).

* cited by examiner

DOSAGE AND ADMINISTRATION FOR PREVENTING CARDIOTOXICITY IN TREATMENT WITH ERBB2-TARGETED IMMUNOLIPOSOMES COMPRISING ANTHRACYCLINE CHEMOTHERAPEUTIC AGENTS

CROSS-REFERENCES TO RELATED APPLICATIONS

This application is a continuation of U.S. patent application Ser. No. 13/912,167, filed Jun. 6, 2013, which is a continuation of PCT Application No.: PCT/US2011/063623, filed Dec. 6, 2011, which claims the benefit under 35 U.S.C. §119 to U.S. Provisional Patent Application No. 61/420,225, filed Dec. 6, 2010; 61/420,688, filed Dec. 7, 2010; and 61/449,602, filed Mar. 4, 2011. The contents of each of the foregoing applications are incorporated herein by reference in their entirety.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Anthracyclines have been an effective backbone of cancer therapies for decades. Despite consistent clinical benefit observed with anthracycline-based regimens in breast cancer, significant toxicities such as acute and/or chronic cardiac dysfunction associated with such treatment have limited more expansive therapeutic use. While liposomal doxorubicin formulations have succeeded in reducing cardiotoxicity to some extent, they have failed to demonstrate clear-cut efficacy advantages and can involve other toxicities such as palmar-plantar erythrodysesthesia (hand foot syndrome). In an effort to improve upon efficacy of currently available anthracyclines, a new immunoliposomal formulation, MM-302, has been prepared that targets doxorubicin to HER2 (ErbB2)-overexpressing tumor cells. Antibody fragments that bind to HER2 without blocking HER2-mediated signaling are coupled to the outer surface of pegylated liposomal doxorubicin.

Doxorubicin (dox) is an anthracyline chemotherapeutic agent used to treat a variety of cancers. The use of doxorubicin is dose-limited by the cardiotoxicity of the drug. In order to address this problem, doxorubicin has been formulated as a pegylated liposomal preparation. Liposomal encapsulation of drugs enables delivery of potent cytotoxic drugs with an improved therapeutic index or therapeutic window. doxorubicin HCl liposome injection (DOXIL®) is a pegylated liposome-encapsulated (liposomal) form of doxorubicin. DOXIL is a commercial form of pegylated liposomal doxorubicin (PLD). DOXIL alters the tissue distribution and pharmacokinetic profile of doxorubicin. Use of DOXIL results in a significantly lower rate of left ventricular cardiac dysfunction and symptomatic congestive heart failure as compared to therapy with free doxorubicin, both alone and in combination with trastuzumab in anthracycline-naïve and previously treated patients. DOXIL® is approved for use to treat Kaposi's sarcoma, ovarian cancer, and multiple myeloma. Doxorubicin HCl liposome injection is also sold as CAELYX®.

Immunoliposomes are antibody (typically antibody fragment) targeted liposomes that provide advantages over non-immunoliposomal preparations because they are selectively internalized by cells bearing cell surface antigens targeted by the antibody. Such antibodies and immunoliposomes are described, for example, in the following US patents and patent applications: US 2010-0068255, U.S. Pat. Nos. 6,214,388, 7,135,177, and 7,507,407 ("Immunoliposomes that optimize internalization into target cells"); U.S. Pat. No. 6,210,707 ("Methods of forming protein-linked lipidic microparticles and compositions thereof"); U.S. Pat. No. 7,022,336 ("Methods for attaching protein to lipidic microparticles with high efficiency") and US 2008-0108135 and U.S. Pat. No. 7,244,826 ("Internalizing ErbB2 antibodies."). The following US and international patents and patent applications describe assays, cell lines, and related technologies that are relevant to this disclosure: U.S. Pat. No. 7,846,440 ("Antibodies against ErbB3 and uses thereof") and U.S. Ser. No. 12/757,801, PCT/US2009/040259, and PCT/US2009/60721 ("Human Serum Albumin Linkers and Conjugates Thereof").

Immunoliposomes targeting ErbB2 (HER2) can be prepared in accordance with the foregoing patent disclosures. Such HER2 targeted immunoliposomes include MM-302, which comprises the F5 anti-HER2 antibody fragment and contains doxorubicin. MM-302 contains 45 copies of mammalian-derived F5-scFv (anti-HER2) per liposome. The F5-scFv was selected for its ability to internalize while not affecting HER2 signaling. Characterization of the F5-scFv indicates that it does not cross react with mouse, rat or rabbit HER2 and does not interfere with HER2 signaling in the free scFv form. Because cardiomyocytes are known to express HER2, concerns have been expressed regarding the potential cardiotoxicity of MM-302 and related HER2-targeted immunoliposomes.

Dosage and Administration of Commercially Available Liposomal Doxorubicin:

DOXIL® (doxorubicin HCl liposome injection) is an exemplary liposomal anthracycline chemotherapeutic drug. DOXIL is typically administered intravenously at a dose indicated in $mg/m^2$ and characterized as doxorubicin HCl equivalent (dox equiv., meaning the total mass of doxorubicin in each dose). Each dose is typically administered at an interval measured in weeks, to yield a dosage of x $mg/m^2$ (dox equiv.) every y weeks. The first liposomal doxorubicin dose is typically administered at an initial rate of 1 mg/min to minimize the risk of infusion-related reactions. If no infusion-related adverse reactions are observed, the infusion rate is typically increased to complete the administration of the drug over one hour.

Patients with Ovarian Cancer:

DOXIL is typically administered to ovarian cancer patients intravenously at a dose of 50 $mg/m^2$ dox equiv. The patient is typically dosed once every 4 weeks, for as long as the patient does not progress, shows no evidence of cardiotoxicity and continues to tolerate treatment. A minimum of 4 courses is recommended because median time to response in clinical trials was 4 months. To manage adverse reactions such as hand-foot syndrome (HFS), stomatitis, or hematologic toxicity the doses may be delayed or reduced. Pretreatment with or concomitant use of antiemetics should be considered.

Patients with AIDS-Related Kaposi's Sarcoma (KS):

DOXIL is typically administered to KS patients intravenously at a dose of 20 mg/m$^2$ (dox equiv.). In KS patients the dose is typically repeated once every three weeks, for as long as patients respond satisfactorily and tolerate treatment.

Patients with Multiple Myeloma:

To treat patients with multiple myeloma, DOXIL is administered with VELCADE® (bortezomib). Bortezomib is administered at a dose of 1.3 mg/m$^2$ as intravenous bolus on days 1, 4, 8 and 11, every three weeks. DOXIL is typically administered to these patients at a dose of 30 mg/m$^2$ as a 1-hr intravenous infusion following each day 4 bortezomib administration. Patients are typically treated for up to 8 cycles until disease progression or the occurrence of unacceptable toxicity.

HERCEPTIN® (trastuzumab) is a therapeutic anti-HER2 antibody that is very widely used to treat HER2 overexpressing tumors. A key dosage-limiting effect of trastuzumab is cardiotoxicity. Cardiomyocytes are known to express HER2, and trastuzumab-mediated cardiotoxicity is generally accepted as being caused by damage to HER2-expressing cardiomyocytes resulting from trastuzumab binding to the cardiomyocyte-expressed HER2—see, e.g., Hysing J and Wist E, "Cardiotoxic Effects of Trastuzumab,". Tidsskr Nor Laegeforen, 2011 Nov. 15; 131(22):2239-2241. Anthracycline drugs such as doxorubicin are known to exert dose-limiting cardiotoxic effects, which are considered a major limitation in their use—see, e.g., Sawyer et al., "Mechanisms of Anthracycline Cardiac Injury: Can we identify strategies for cardio-protection?" Prog Cardiovasc Dis., 2010 September-October; 53(2):105-13.

Doxorubicin-induced cardiac damage is irreversible, resulting in acute injury and also damage that can manifest itself years after treatment. Exposure to cumulative concentrations of doxorubicin above 550 mg/m$^2$ increases the potential for cardiomyopathy and heart failure. The development of HER2-directed therapy for the treatment of HER2-positive breast cancer has led to the investigation of the clinical benefit of the combination of doxorubicin and trastuzumab. The clinical efficacy of doxorubicin plus trastuzumab was superior to that of paclitaxel plus trastuzumab; however, there was an increased incidence of cardiac toxicity observed on the doxorubicin plus trastuzumab arm of the study, and the combination was not approved for marketing. The clinical benefit of anthracycline-based therapy, specifically in HER2-positive breast cancer, remains controversial.

Liposomal encapsulation of drugs has enabled delivery of potent cytotoxic drugs with an improved therapeutic index. Pegylated liposomal doxorubicin (PLD) alters the tissue distribution and pharmacokinetic profile of doxorubicin. PLD has demonstrated a significantly lower rate of left ventricular cardiac dysfunction and symptomatic congestive heart failure as compared to therapy with conventional doxorubicin, alone and in combination with trastuzumab in anthracycline-naive and previously treated patients. A proposed mechanism for the reduced cardiotoxicity of PLD is that its greater size relative to conventional doxorubicin prevents it from crossing the endothelial barrier in the heart, thereby minimizing doxorubicin exposure to heart tissue.

MM-302 is a HER2-targeted, pegylated liposome designed to deliver doxorubicin directly to HER2-overexpressing cancers. HER2-targeted PLD deposits in tumors through the enhanced permeability and retention effect similar to PLD. In the tumor microenvironment, targeting HER2-overexpressing cells with HER2-targeted PLD results in superior efficacy relative to PLD in preclinical models. During the development of MM-302, concern was expressed by regulatory authorities that due to its HER2-targeting, MM-302 would deliver cardiotoxic doxorubicin directly to cardiomyocytes, resulting in increased cardiotoxicity compared to doxorubicin HCl liposome injection, and reduced dosages of MM-302 were suggested to avoid such life-threatening toxicities.

BRIEF SUMMARY OF THE INVENTION

The present invention provides methods to determine safe doses and to safely use anti-HER2 immunoliposomal anthracyclins to treat HER2-expressing cancers, e.g., without increased risk of cardiotoxicity as compared to doxorubicin HCl liposome injection (DOXIL), and provides other advantages.

It has now been discovered that anti-ErbB2 targeted, anthracycline-containing immunoliposomes, e.g., MM-302, are not any more cardiotoxic than doxorubicin HCl liposome injection (DOXIL®), and can be dosed using exactly the same dosages, (i.e., dose and administration amounts and schedules) as used for doxorubicin HCl liposome injection without any increase in cardiotoxicity risk or decrease in efficacy. Furthermore, it has now been demonstrated that MM-302 can be effectively targeted to cells expressing 200,000 or more ErbB2 (HER2) receptors per cell in vitro and in vivo, indicating that it can be used to treat patients with HER2-overexpressing tumors that are either HER2 "3+" (e.g., by HERCEPTEST®), HER2 FISH+ (fluorescence in situ hybridization for HER2 gene amplification) or HER2 "2+" (e.g., by HERCEPTEST).

Therefore, disclosed herein are methods for determining a safe and effective dosage for use in treating a human cancer patient by administration of anthracycline-comprising anti-HER2 immunoliposomes, the patient being diagnosed with a cancer characterized by expression of HER2 receptor, the methods comprising determining a first dosage, such a dosage indicating a dose magnitude and frequency of dosing, for a patient diagnosed with a cancer characterized by expression of HER2 receptor, the first dosage being for a liposomal anthracycline chemotherapeutic agent that does not comprise an immunoliposome, which dosage is determined to provide to the patient a safe and effective amount of the liposomal anthracycline chemotherapeutic agent; and determining a dosage for the administration of the anthracycline-comprising anti-HER2 immunoliposomes, a plurality of which immunoliposomes is each bearing a plurality of anti-HER2 antibody molecules on its surface and each containing the anthracycline chemotherapeutic agent, where the safe and effective dosage for the administration of the anthracycline-comprising anti-HER2 immunoliposomes is the first dosage.

Also disclosed are methods of treating a human cancer patient by administration of anthracycline-comprising anti-HER2 immunoliposomes, the methods comprising determining a first dosage, such a dosage indicating a dose magnitude and frequency of dosing, for a patient diagnosed with a cancer characterized by expression of HER2 receptor, the first dosage being for a liposomal anthracycline chemotherapeutic agent that does not comprise an immunoliposome, which dosage is determined to provide to the patient a safe and effective amount of the liposomal formulation, and administering anthracycline-comprising anti-HER2 immunoliposomes, a plurality of which immunoliposomes is each bearing a plurality of anti-HER2 antibody molecules on its surface and each containing the anthracycline chemotherapeutic agent, where the anthracycline-comprising anti-HER2 immunoliposomes are administered to the patient at the first dosage.

In certain aspects the anthracycline is doxorubicin. In other aspects the liposomal anthracycline chemotherapeutic agent that does not comprise an immunoliposome is doxorubicin HCl liposome injection and the HER2-targeted immunoliposomes are MM-302. In others, the cancer is breast cancer, Kaposi's sarcoma, ovarian cancer, or multiple myeloma. In yet other aspects, the first dosage is 50 mg/m$^2$, 40 mg/m$^2$, 30 mg/m$^2$, 20 mg/m$^2$, or 10 mg/m$^2$ every two weeks or every three weeks or every four weeks. In other aspects the cancer characterized by expression of HER2 receptor is further characterized as being HER2$^{2+}$, HER2$^{3+}$, or HER2 FISH positive. In others the cancer characterized by expression of ErbB2 receptor is further characterized as expressing an average of at least 200,000 cell surface ErbB2 receptors per cell. In yet others, the administration of the immunoliposomes at the first dosage is effective to treat the cancer and in others the administration of the immunoliposomes at the first dosage does not result in increased cardiotoxicity as compared to administration at the first dosage of the liposomal anthracycline chemotherapeutic agent that does not comprise an immunoliposome. In other aspects, the administration of the immunoliposomes to the patient at the first dosage results in a peak concentration of the immunoliposomes in the patient's bloodstream, and treating human cardiomyocytes in vitro by culturing in medium comprising the immunoliposomes at about the peak concentration does not reduce, or reduces by no more than 5%, heregulin-stimulated increase of pERK or pAKT in the cultured cardiomyocytes as compared to in control human cardiomyocytes cultured in medium free of the immunoliposomes. In other aspects the immunoliposome concentration in the patient's bloodstream is measured as a serum immunoliposome concentration. In yet other aspects each of the HER2 immunoliposomes bears on its surface, on average, 45 anti-HER2 antibody molecules.

DETAILED DESCRIPTION OF THE INVENTION

Figure 1A:
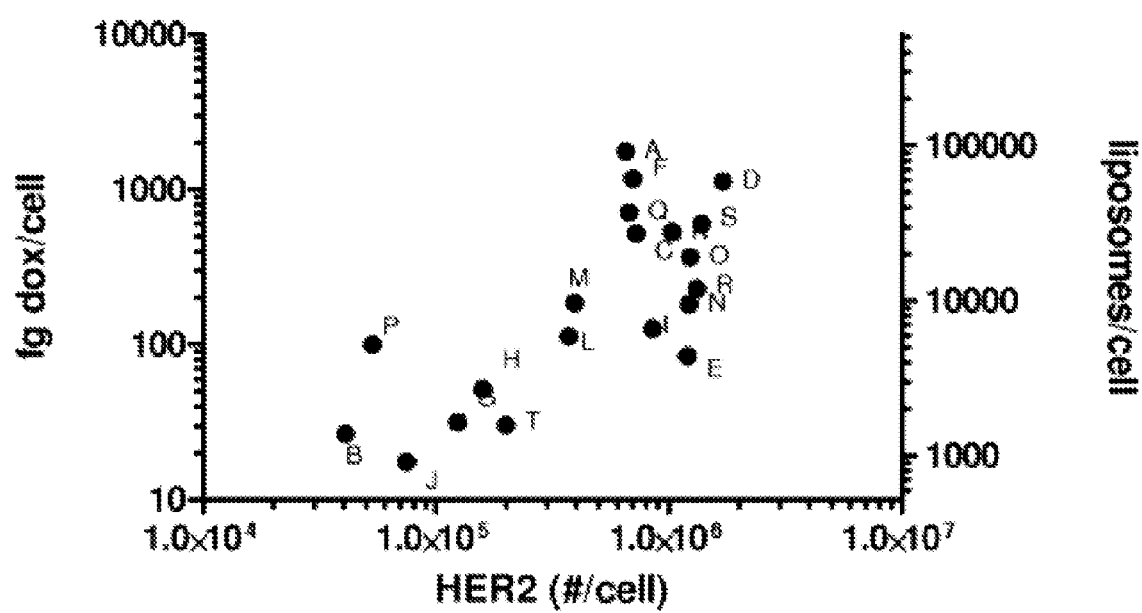
FIG. 1A depicts a graph of the expression of HER2 in multiple cell lines after being treated with 15 μg/ml of MM-302 immunoliposomes containing doxorubicin (dox) for 2 hr and levels of total cellular doxorubicin internalized as determined using HPLC. The y-axes represent femtograms dox per cell (left) and liposomes per cell (right) and the x-axes represent the number of HER2 receptors per cell (log scale).

An MM-302 liposome is a unilamellar lipid bilayer vesicle of approximately 75-110 nm in diameter that encapsulates an aqueous space which contains doxorubicin in a gelated or precipitated state. The lipid membrane is composed of phosphatidylcholine, cholesterol, and a polyethyleneglycol-derivatized phosphatidylethanolamine in the amount of approximately one PEG molecule for 200 phospholipid molecules, of which approximately one PEG chain for each 1780 phospholipid molecules bears at its end an F5 single-chain Fv antibody fragment that binds to HER2. MM-302 liposomes are prepared from HSPC (Hydrogenated soy phosphatidylcholine):Cholesterol (plant-derived):PEG-DSPE (polyethylene glycol-disteroylphosphoethanolamine) at a molar ratio of 3:2:0.3. The total HSPC lipid concentration of MM-302 is about 40 mmol/L. MM-302 contains about 10 mmol/L of lipid, and about 2 mg/mL of doxorubicin. MM-302 comprises 1.8-2.2 mg/mL of doxorubicin in liposomes that contain 0.16-0.30 mg/mL DSPE-PEG-F5 (prepared as described in U.S. Pat. No. 6,210,707). F5 is an anti-ErbB2 (HER2) scFv antibody fragment (encoded by ATCC plasmid deposit designation PTA-7843). MM-302 liposomes comprise 130-170 g doxorubicin/mol phospholipid and 12-22 g F5-PEG-DSPE/mol phospholipid. MM-302 is formulated in sterile 10 mM/L histidine-HCl as a buffer (pH 6.5), and 10% sucrose to maintain isotonicity. MM-302 liposomes are loaded using pre-loaded ammonium sulfate MM-302 Dosing

| | Dose 1 | Dose 2 | Dose 3 | Dose 4 | Dose 5 |
|---|---|---|---|---|---|
| Every week | 10 mg/m$^2$ | 20 mg/m$^2$ | 30 mg/m$^2$ | 40 mg/m$^2$ | 50 mg/m$^2$ |
| Every two weeks | 10 mg/m$^2$ | 20 mg/m$^2$ | 30 mg/m$^2$ | 40 mg/m$^2$ | 50 mg/m$^2$ |
| Every three weeks | 10 mg/m$^2$ | 20 mg/m$^2$ | 30 mg/m$^2$ | 40 mg/m$^2$ | 50 mg/m$^2$ |
| Every four weeks | 10 mg/m$^2$ | 20 mg/m$^2$ | 30 mg/m$^2$ | 40 mg/m$^2$ | 50 mg/m$^2$ |
| Every five weeks | 10 mg/m$^2$ | 20 mg/m$^2$ | 30 mg/m$^2$ | 40 mg/m$^2$ | 50 mg/m$^2$ |

"mg/m²" indicates mg of doxorubicin (formulated as MM-302) per square meter of body surface area of the patient. For breast cancer, dose 3, 4, or 5 is preferred. For Kaposi's sarcoma dose 1, 2, or 3 is preferred, for ovarian cancer, dose 3, 4, or 5 is preferred and for multiple myeloma dose 2, 3, 4, or 5 is preferred. Dosing regimens may vary in patients with solid tumors that are "early" (pre-metastatic, e.g., adjuvant breast cancer) as compared to "advanced" (metastatic tumors).

Preferred tumors are those in which the tumor cells overexpress HER2. A tumor that overexpresses HER2 is one that is identified as being HER2 "3+" or HER2 "2+" by HercepTest™, or HER2 FISH+ by fluorescence in situ hybridization. Alternatively, a preferred tumor that overexpresses HER2 is one that expresses an average of 200,000 or more receptors per cell, as quantified by the methods described in the Examples.

MM-302 Therapy of Advanced Breast Cancer

MM-302 is administered once every 4 weeks by intravenous (IV) infusion over 60 minutes at 8, 16, 30, 40, or 50 mg/m² to patients with locally advanced/unresectable or metastatic advanced breast cancer that overexpresses HER2 as determined by FISH or by IHC or by determination of the average number of HER2 receptors per cell. Patients should have adequate bone marrow reserves as evidenced by: 1) absolute neutrophil count (ANC)≥1,500/µL; 2) platelet count≥100,000/µL and 3) hemoglobin≥9 g/dL (Transfusions allowed). Patients should have adequate hepatic function as evidenced by: 1) serum total bilirubin≤1.5×ULN and 2) Aspartate aminotransferase (AST), Alanine aminotransferase (ALT) and Alkaline Phosphatase (ALP) normal or up to 2.5×upper limit of normal (ULN; 5×ULN is acceptable for ALP if liver metastases and/or bone metastases are present). Patients should have adequate renal function as evidenced by a serum creatinine≤1.5×ULN. Patients should be recovered from any clinically relevant toxic effects of any prior surgery, radiotherapy or other therapy intended for the treatment of breast cancer. Women of childbearing potential as well as fertile men and their partners must be warned to abstain from sexual intercourse or to use an effective form of contraception during treatment and for 90 days following the last dose of MM-302. Patients should have adequate cardiac function as evidenced by a measured left ventricular ejection fraction of ≥50% by ECHO or MUGA within approximately 30 days of treatment. Patients who are pregnant or lactating and those with NYHA Class III or IV congestive heart failure or left ventricular ejection fraction (LVEF)<50%, or a prolonged QTc interval (≥460 ms), are preferably not be treated with MM-302.

The following Examples are merely illustrative and should not be construed as limiting the scope of this disclosure in any way as many variations and equivalents will become apparent to those skilled in the art upon reading the present disclosure.

EXAMPLES

Materials and Methods Used in these Examples

Materials:
Doxorubicin is from SIGMA-ALDRICH, Inc. (St. Louis, Mo.). FITC-conjugated lectin (*lycopersicon esculentum* (tomato) lectin, Cat #FL-1171) is purchased from Vector Laboratories, Inc. (Burlingame, Calif.). Acetic acid, Methanol, and Acetonitrile are from EMD Chemicals Inc. (Gibbstown, N.J.). Water and Trifluoroacetic Acid (TFA) are from J. T. Baker (Phillipsburg, N.J.). HOECHST 33342 trihydrochloride trihydrate, ProLong Gold®, and DiIC18(5)-DS (DiI5) are from Invitrogen (Carlsbad, Calif.). Cholesterol and 1,2-distearoyl-sn-glycero-3-phosphoethanolamine-N-[amino (polyethylene glycol)-2000] (ammonium salt) (PEG-DSPE) are from Avanti Polar Lipids Inc. Hydrogenated soy phosphatidylcholine (HSPC) is from Lipoid (Newark, N.J.). RPMI is from Lonza (Walkersville, Md.), Fetal Bovine Serum (FBS) is from Tissue Culture Biologicals and penicillin G/streptomycin sulphate mixture is from GIBCO (Invitrogen).

Preparation of Immunoliposomes:
Liposomes are prepared and loaded with doxorubicin using an ammonium sulfate gradient as previously described (Kirpotin et. al., Cancer Res. 2006; 66:6732-40; Park et al., Clin Cancer Res. 2002; 8:1172-81). The lipid components are HSPC, cholesterol, and PEG-DSPE (3:2:0.3, mol:mol:mol). The anti-ErbB2 (F5)-PEG-DSPE conjugate is prepared and inserted into the liposome to form immunoliposomes as reported by Nellis et al., (Biotechnol Prog. 2005; 21:205-20; Biotechnol Prog. 2005; 21:221-32). The DiI-5-labelled liposomes, MM-302-DiI5 and PLD-DiI5, are prepared as above with the difference that the DiIC18(5)-DS (DiI5) dye is solubilized with the lipid components at a concentration of 0.3 mol % of total phospholipid. In all cases unloaded free doxorubicin is removed using a Sephadex® G-75 size exclusion column eluted with Hepes buffered saline (pH 6.5). F5-lipo-DiI5 is prepared in a similar fashion as above but without doxorubicin, and incorporating an aqueous solution of HEPES buffered saline (pH 6.5).

Tumor Cell Culture:
BT474-M3 cells (see Noble, Cancer Chemother. Pharmacol. 2009 64:741-51), are HER2-overexpressing human breast cancer cells. BT474-M3 cells are grown in RPMI medium containing 10% FBS and 1% penicillin G/streptomycin sulphate. Embryonic stem cell-derived (ESCd) cardiomyocytes are obtained from P. W. Zandstra, Institute of Biomaterials and Biomedical Engineering, University of Toronto, Toronto, Ontario, Canada; (Bauwens et al., Tissue Eng Part A. 2011 Apr. 25, PMID 21417693;). These cells have been shown to express appropriate cellular markers of cardiomyocytes such as LIM domain homeobox gene Isl-1, Troponin T, and Myosin Light Chain 2c. The percentage of Troponin T positive cells is determined following differentiation. Batches containing less than 70% positive for Troponin T are discarded. Induced pluripotent stem cell-derived (iPSd) cells are obtained from Cell Dynamics International and are handled per the manufacturer's protocol.

Xenograft Studies:
5-7-week-old female nude mice are purchased from Charles River Laboratories or Taconic Farms, Inc (NCr nude mice). Unless otherwise indicated, mice are inoculated with BT474-M3 breast cancer cells or NCI-N87 gastric cancer cells (NCI-DTP, 10×10⁶ cells in 100 µl RPMI) into the right dorsal flank of the mice (subcutaneous injection, s.c.). When the tumors reach an average volume of ~200 mm³, studies are performed as described below.

Testing of Tumor HER2 Levels:
Homozygous NCr nude mice are inoculated with 15×10⁶ BT474-M3 cells in the mammary fat pad 2nd from the top right hand side. BT474-M3 tumors are injected with a single dose of 4 mg/ml fluorescently-labeled (with DiI5 as described below) HER2-targeted or untargeted liposomes without doxorubicin. Twenty-four hours later, the tumors are excised and dissociated by mechanical and enzymatic means. After surface staining with anti-HER2 cells are analyzed by flow cytometry on a FACSCalibur™ instrument (BD Biosciences). The flow cytometry dataset is analyzed for the relationship between HER2 surface expression levels and uptake of liposomes above a given threshold by plotting the overall percentage of cells with elevated liposome content in narrowly gated cell subsets defined by increasing HER2 signals.

Single Cell Distribution of Cell Surface HER2:

BT474-M3 tumor xenograft tissue is stained with an anti-HER2 antibody and counterstained with DAPI. The slide is imaged with an Aperio® Scanscope® at 20× magnification and the image is analyzed. The intensity of the HER2 membrane staining is quantified on a single-cell basis as the (mean of the inner border of the HER2 layer)+(mean of the outer border of the HER2 layer).

Efficacy Study:

Mice are randomized into three treatment groups (n=7/group) based on an average tumor volume from mice that receive PBS (control), MM-302 or PLD, dosed at 3 mg/kg (q7d, n=3 total doses). Tumors are measured twice/week with a caliper. Tumor volumes are calculated using the formula: width$^2$×length×0.52. Mice are weighed twice/week to monitor weight loss.

Uptake of Liposomes in HER2-Expressing Cell Lines:

Multiple cell lines expressing various levels of HER2 are treated with 15 µg/ml of MM-302 or PLD for 2 h and total cellular doxorubicin is quantified by HPLC. Murine 4T1 breast cancer cells and human HeLa cervical cancer cells are obtained from the ATCC and propagated according to ATCC recommendations. Cells are characterized for human HER2 expression by flow cytometry using a commercial anti-HER2 antibody (BD Biosciences #340552). This antibody does not cross-react with murine HER2 but detects human HER2. A neomycin-selectable expression vector encoding human HER2 is obtained from GeneCopeia (Z2866). 4T1 and HeLa cells are transfected with this construct using the non-lipid polymer transfection reagent MegaTran® 1.0 (Origene) according to the manufacturer's instructions. Transfected cells are selected with 400-500 µg/ml Geneticin/Neomycin (Invitrogen). Surviving cells are allowed to expand under reduced Geneticin/Neomycin concentrations (100 µg/ml) and are sorted on a BD Biosciences FACSAria™ instrument to obtain enriched cell populations with human HER2 expression exceeding those observed in parental HeLa cells. The sort-enriched cells are then sub-cloned by limited dilutions, and colonies are ranked by HER2 surface levels to obtain representative populations of 4T1 and HeLa cells that express different ranges of HER2. Fluorescent intensity of HER2 surface staining measured by flow cytometry is compared to staining with the same antibody bound to Quantum™ Simply Cellular® anti-mouse IgG microspheres (Bangs Laboratories #815) according to the manufacturer's instructions to calculate the number of HER2 surface receptors of the cells.

Figure 8A:
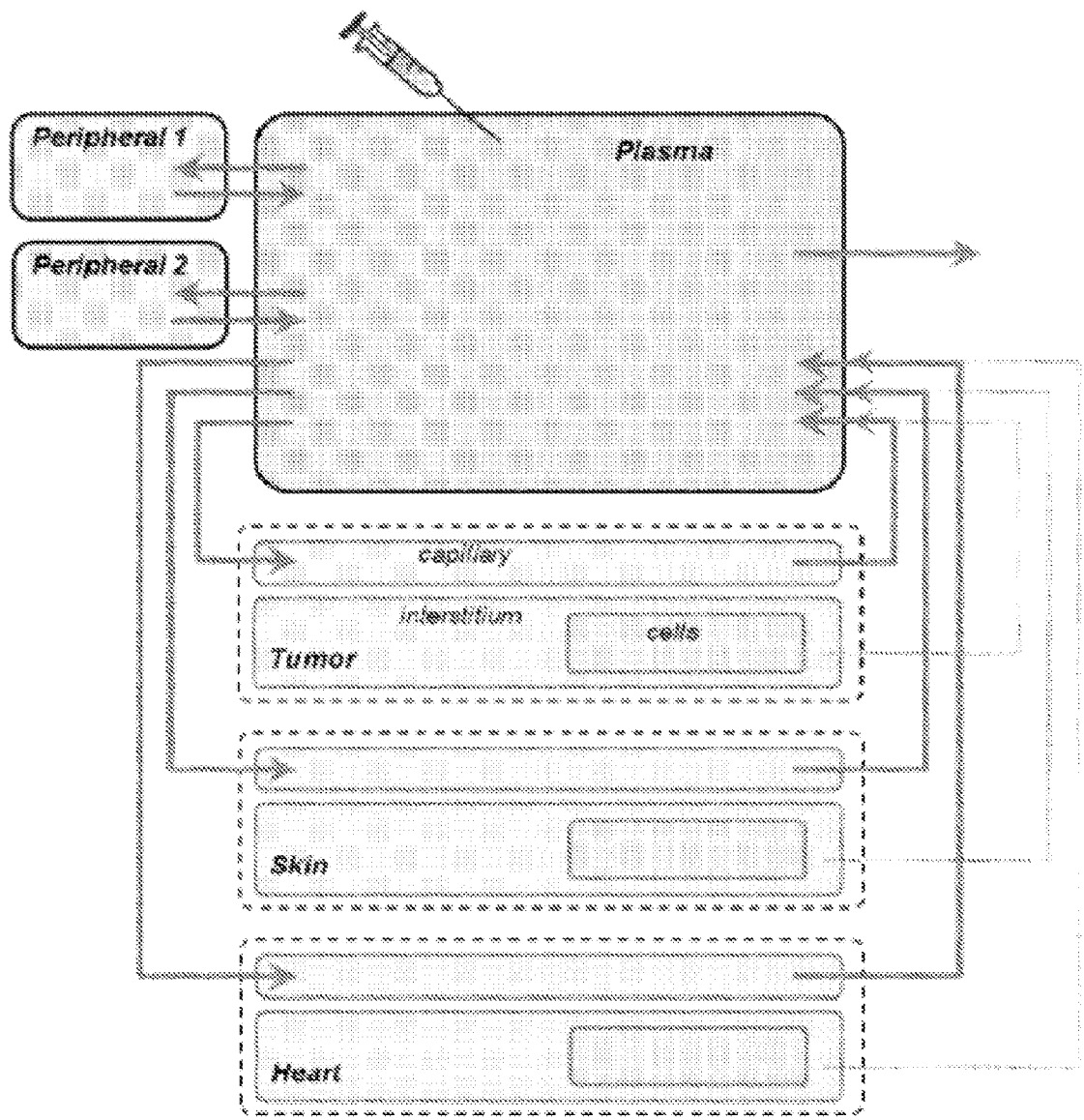
FIG. 8A depicts a graphical illustration of a computational model developed and calibrated on literature and in-house data for free and liposomal doxorubicin. The model can be applied to understand the competing kinetic processes that determine drug concentration and exposure for liposomal versus free doxorubicin in various tissues.
Figure 8B:
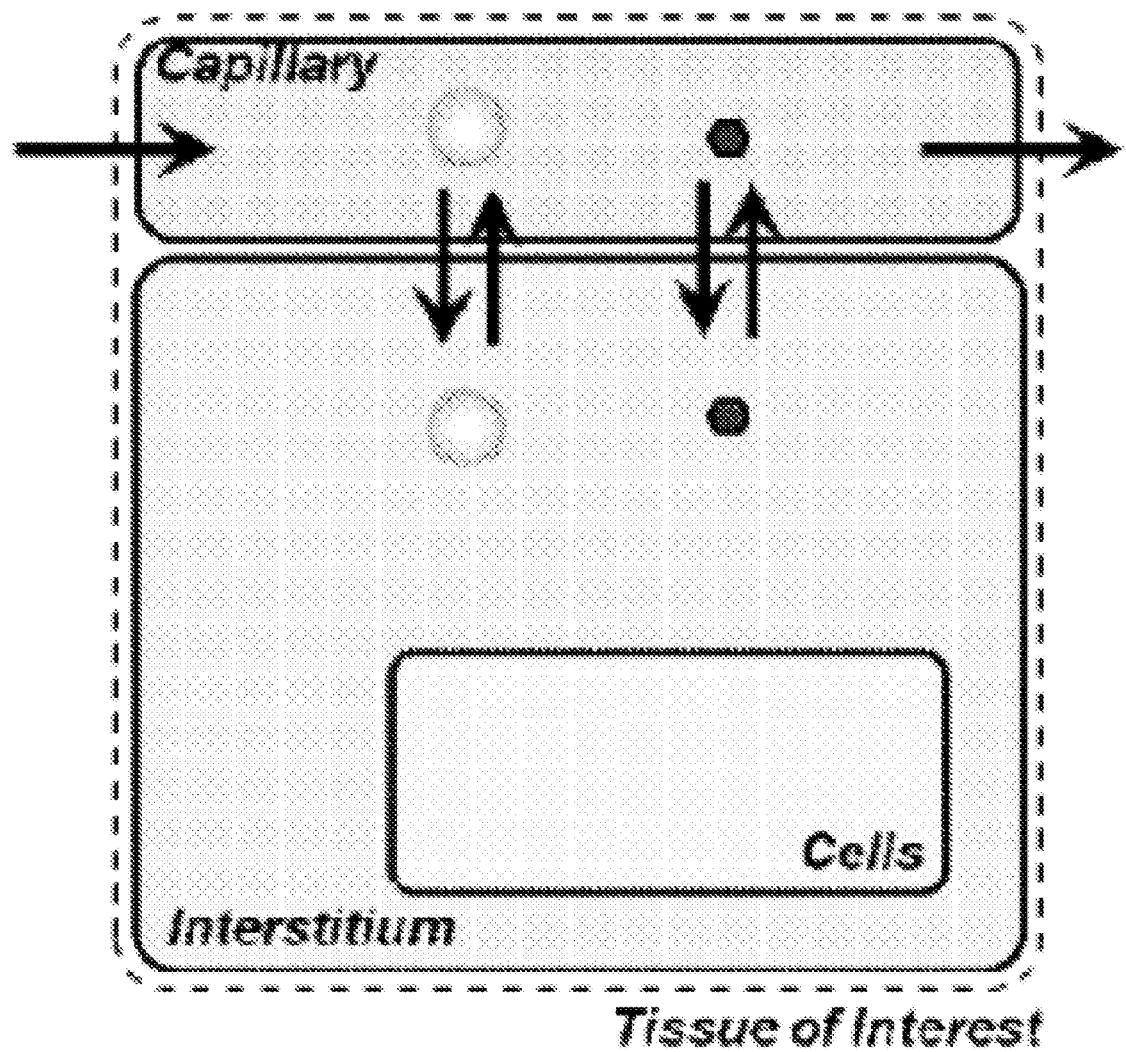
FIG. 8B depicts a graphical illustration of a computational model developed and calibrated on literature and in-house data for tissue deposition of free and liposomal doxorubicin in mouse.
Figure 8C:
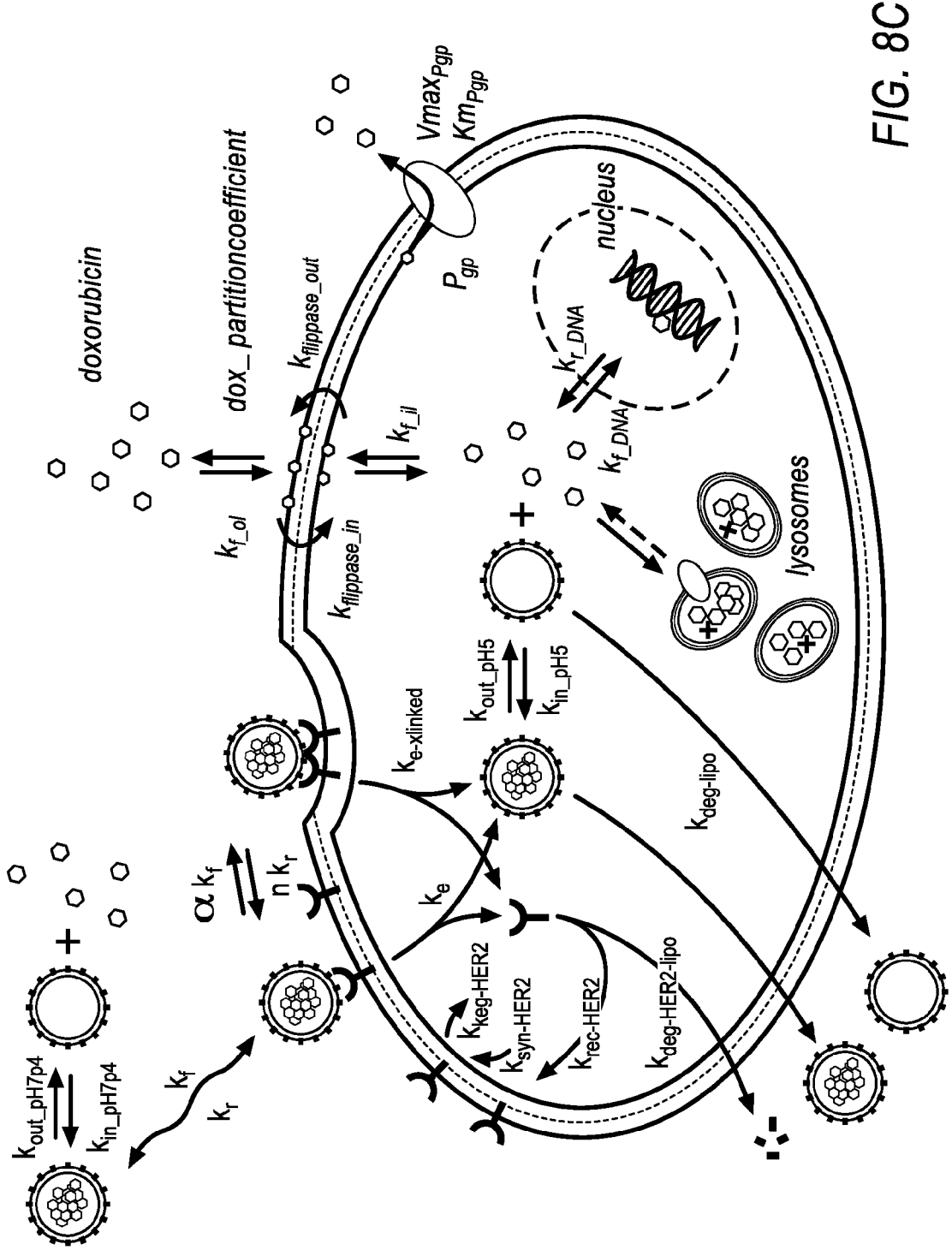
FIG. 8C depicts a graphical illustration of a theoretical kinetic model to provide a framework for understanding the role of HER2 expression in MM-302 uptake and doxorubicin cellular trafficking.

Uptake of Liposomes in Cardiomyocytes:

iPSd cardiomyocytes are plated per the manufacturer's instructions (Cell Dynamics International Cat #CMC-100-110-001) in a 24-well tissue culture plate at 250,000 cells/well. Two days later, the 0.5 ml of media in the wells is removed and replaced with 0.5 ml of 15.0 µg/ml (dox equiv.) of MM-302, PLD or free doxorubicin. The plates are swirled in a "figure 8 fashion" 20 times to maximize exposure of the cells to the liposomes. Cells are incubated with MM-302, PLD or free doxorubicin for the indicated time period after which the media are removed and the cells are washed once with 0.5 ml of PBS. The PBS is removed and 0.5 ml of 0.05% trypsin is added to each well. The cells are monitored, and once detachment begins, 0.5 ml of medium containing FBS is added to each well to inactivate the trypsin. The cells are collected and placed in microcentrifuge tubes. The cells are spun at 1,500 rpm for 5 minutes at 4° C. The cell pellet is resuspended by vortexing and pipetting in 0.5 ml of 1.0% acetic acid in methanol and placed at –80° C. for 1 hour to extract the doxorubicin. The microcentrifuge tube containing the resuspended cell pellet is spun at 10,000 rpm for 10 minutes in the cold room, and 450 µl of the supernatant is transferred to a HPLC tube. Samples are run on the HPLC machine and concentration per sample is determined by relating values to a doxorubicin standard curve.

Biodistribution of Liposomes:

Mice are randomized into 4 groups that received a single intravenous (i.v.) dose of either PBS, doxorubicin, MM-302-DiI5 or PLD-DiI5 (all at 3 mg/kg), respectively. Mice (n=4/time point/group) are sacrificed at 0.5, 4, 24 and 96 h (doxorubicin) or 168 h (MM-302-DiI5 and PLD-DiI5) after the single dose. Five minutes before sacrificing, mice are injected i.v. with 100 µl of FITC-lectin, to label the vasculature.

HPLC Quantification of Doxorubicin:

Heart tissues are weighed and disaggregated with 1 mL $H_2O$ using a TissueLyser™ (Qiagen) for 3 min. 100 µl of the homogenate is then transferred into a new tube and 900 µl of 1% acetic acid/methanol is added. For the cultured cells, cells are treated with drug, as described above, trypsinized and lysed using 1.0% acetic acid in methanol. Lysates are vortexed for 10 sec. and placed at –80° C. for 1 h. Samples are spun at room temperature (RT) for 10 min at 10,000 RPM. Supernatants and doxorubicin standards are analyzed by HPLC (Dionex) using a C18 reverse phase column (Synergi™ POLAR-RP® 80 Å, 250×4.60 mm 4 µm column). Doxorubicin is eluted running a gradient from 30% acetonitrile; 70% 0.1% trifluoroacetic acid (TFA)/$H_2O$ to 55% acetonitrile; 45% 0.1% TFA/H2O during a 7 min span at a flow rate of 1.0 ml/min. The doxorubicin peak is detected at 6.5 min using an in-line fluorescence detector excited at 485 nm, and emitting at 590 nm. The extraction efficiency of doxorubicin from the heart tissue was 83% as determined by a control heart spiked with a known amount of doxorubicin.

Confocal Microscopy and Image Analysis of Heart Snap-Frozen Sections:

10 µm-thick heart sections are air-dried for 30 min at RT, counterstained with Hoechst® 33342 diluted 1:10,000 in mounting media (ProLong® Gold, Invitrogen) and mounted. Slides are imaged on a LSM 510 Zeiss® confocal microscope equipped with Enterprise (351, 364 nm), Argon (458, 477, 488, 514 nm), HeNe1 (543 nm) and HeNe2 (594 nm) lasers with a Plan-Neofluar® 40×/1.3 oil DIC objective. Image analysis and quantification of nuclear doxorubicin is carried out using Definiens® Developer XD™ (Definiens, Parsippany, N.J.). Nuclei are segmented in the Hoechst channel. Doxorubicin positive nuclei are segmented in the doxorubicin channel. The percentage of doxorubicin positive nuclei is quantified as a ratio of the number of objects in the doxorubicin channel divided by the total nuclei objects in the Hoechst channel.

Receptor Quantification:

Stem cell-derived cardiomyocytes are trypsinized, washed, and HER2 levels are determined as described above under "Uptake of liposomes in HER2-expressing cell lines."

Viability:

ESCd cardiomyocytes are treated for 3 h at the indicated concentrations of MM-302, PLD and doxorubicin. Cells are washed twice with PBS, fresh medium is added and the cells are incubated for an additional 24 h. Cell viability is assessed using CellTiter-Glo® from Promega (Madison, Wis.) and the percent of viable cells is determined relative to the untreated population.

Troponin I ELISA:

15,000 iPSd (iCELL®) cardiomyocytes (Cellular Dynamics International, Madison Wis.) cells are plated per the manufacturer's protocol. Cells are treated for 24 h with the indicated concentrations of free doxorubicin, PLD or MM-302. The supernatant is collected and analyzed using a human Troponin I ELISA (Catalog #: GWB-83A61F, Genway Biotech, San Diego Calif.) per the manufacturer's protocol. A PrestoBlue® Cell Viability Assay (Catalog #: A-13261, Invitrogen, Grand Island, N.Y.) is performed on the remaining cells in 100 µl per the manufacturer's protocol.

High-Content Analysis:

Cardiomyocytes are treated as described above. Cells are fixed using 3.7% formaldehyde, washed twice with PBS containing 0.1% Tween-20 (PBS-T), and permeabilized with methanol. Cells are blocked using a 1:1 mixture of LI-COR® Odyssey® Blocking Buffer (Lincoln, Nebr.) and PBS-T for 1 h at room temperature (RT). Cells are stained with a 1:400 dilution of the indicated primary antibody from Cell Signaling Technology (Beverly, Mass.) and incubated shaking at 4° C. overnight. Cells are washed and incubated with a 1:2,000 dilution of the fluorescently labeled secondary antibody for 1 h at RT. Cells are stained with a 1:10,000 dilution of Hoechst 33342 and 1:1,000 dilution of Whole Cell Stain from Pierce Protein Research Products (Rockford, Ill.) for 30 min at RT to allow visualization of DNA and the whole cell, respectively. Plates are scanned using the Applied Precision Instruments ArrayWorx® High Content Scanner (Issaquah, Wash.) with a 10× objective for Hoechst 33342/Whole Cell Stain (460 nm), doxorubicin (595 nm), and APC/DiI5 (657 nm). Images are analyzed using the software ImageRail (as described in Millard et al., Nat Methods. 2011; 8:487-92). An intensity threshold is established for nuclear and whole cell signals. This threshold is then applied to all images and used to segment individual cells. Data is presented as the mean pixel intensity for all cells in a given well for the indicated channel.

Signaling in Cardiomyocytes:

iPS-derived cardiomyocytes (iCell™ iPS-derived human cardiomyocytes—Cellular Dynamics International (CDI), Madison, Wis.—CDI #CMC-100-010-001, Lot 1258680) are cultured using iCell™ Plating Medium (CDI #CMM-100-110-005, Lot 1013740 and iCell™ Maintenance Medium (CDI #CMM-100-120-005, Lot 1000305) and are exposed to components of MM-302. Levels of phospho-AKT (pAKT) and phospho-ERK (pERK) in the cardiomyocytes are then measured using immunostaining and high content microscopy. Cells are pretreated for 24 hours with either trastuzumab, lapatinib, or the MM-302 antibody (F5-scFv) and an MM-302 molecule (liposome) not containing doxorubicin (F5-lipo) at an equivalent concentration to 5.0 ug/ml of MM-302. Cells are stained and imaged using high content microscopy as described above for (A) pAKT and (B) pERK following a 10 minute stimulation with 10 nM and 5 nM of heregulin, respectively. The following primary antibodies are used at a 1:400 dilution in blocking buffer: pERK antibody—Cell Signaling Technology (CST—Danvers Mass.)—Catalog 9106L (Phospho-p44/42 MAPK (Erk1/2) (Thr202/Tyr204) (E10) Mouse mAb #9106); pAKT antibody—CST—Catalog 4060L (Phospho-Akt (Ser473) (D9E) XP™ Rabbit mAb #4060). Secondary antibodies are Anti-mouse IgG (H+L), F(ab')2 Fragment (Alexa Fluor® 647 Conjugate)—CST—Catalog 4410; Anti-rabbit IgG (H+L), F(ab')2 Fragment (Alexa Fluor® 647 Conjugate)—CST—Catalog 4414. Whole cell stain and DNA stain (Hoechst 33342) are used as described above. Images are analyzed and individual cells are segmented on the basis of Hoechst 33342 nuclear staining. Single cell signal intensity for each stain is quantified and represented as the mean relative intensity of individual cells.

The results in the following Examples were obtained using the above methods or minor variations thereof. Cellular uptake studies in tumor cell lines expressing various levels of HER2 demonstrate that MM-302 delivers significantly higher doxorubicin levels to HER2 over-expressing tumor cells compared to PLD as well as similar or higher levels than highly permeable free doxorubicin. However, in human cardiomyocytes, while free doxorubicin was again taken up at high levels, doxorubicin uptake was dramatically lower with both MM-302 and PLD. Pharmacokinetic studies in mice demonstrate that MM-302 has a similar half-life, clearance, and organ distribution compared to PLD. In HER2-overexpressing BT474 breast and NCI-N87 gastric tumor xenografts, MM-302 exhibits superior anti-tumor activity to both free anthracyclines and PLD. Tumor microdistribution studies further suggest that differences in the localization of doxorubicin in the tumor may be responsible for the enhanced activity of MM-302 compared to free doxorubicin and PLD.

Example 1

Correlation Between HER2 Expression and MM-302 Uptake in Vitro

The level of cell surface HER2 expression on multiple cell lines was determined as described above. These same cell lines were then treated with 15 µg/ml of MM-302 (FIG. 1A, Table 1) or PLD (FIG. 1B, Table 2) for 180 minutes, after which the cells were collected and the amount of cell associated doxorubicin was quantified by HPLC. By plotting the number of HER2 receptors per cell for each cell line vs. the quantity of doxorubicin present per cell in that same cell line following treatment, a relationship between increasing HER2 levels and increasing doxorubicin becomes evident. Through this representation, there appears to be an inflection point at approximately 200,000 HER2 receptors per cell where cells expressing greater than this number appear to have consistently higher levels of cell associated doxorubicin. Taken together, these results support the specificity of MM-302, with high uptake by cells expressing levels of HER2 above the inflection point (such as HER2 overexpressing cancers) and no-to-minimal uptake in cells expressing levels of HER2 below the inflection point (such as cells in normal tissues, e.g., cardiomyocytes).

TABLE 1

HER2 levels vs MM-302 uptake

| FIG. 1A | Cell line | Source | HER2 (#/cell) | fg dox/cell |
|---|---|---|---|---|
| A | 4T1-clone-12W7 | ATCC # CRL-2539 ™ | 650,000 | 1,758.63 |
| B | ADRr | ATCC # HTB-22 ™ (MCF7 derivative) | 40,792 | 26.47 |
| C | AdRr-Her2 | ATCC # HTB-22 ™, stably transfected with HER2 | 722,000 | 519.04 |
| D | BT474-M3 | Noble, Cancer Chemother. Pharmacol. 2009 64: 741-51 | 1,706,601 | 1,123.51 |
| E | Calu-3 | ATCC # HTB-55 ™ | 1,196,976 | 84.06 |
| F | HCC1954 | ATCC # CRL-2338 ™ | 700,000 | 1,174.60 |
| G | HeLa | ATCC # CCL-2 ™ | 123,713 | 31.61 |
| H | IGROV1 | NCI 60-cell panel from NCI-DTP, DCTD TUMOR REPOSITORY, Operated by Charles River Laboratories, Inc. (NCI-DTP) | 158,418 | 51.54 |
| I | JIMT-1 | DSMZ # ACC-589 | 850,000 | 126.85 |
| J | MCF7 | ATCC # HTB-22 | 74,745 | 17.52 |
| K | MCF7-c18 | Gift from Dr. Christopher Bentz, Director, Cancer and Developmental Therapeutics Program, Buck Institute for Age Research, UCSF | 1,031,247 | 531.31 |
| L | MDA-MB-361 | ATCC # HBT-27 ™ | 371,731 | 112.79 |
| M | MDA-MB-453 | ATCC # HBT-131 ™ | 393,441 | 185.51 |
| N | MKN-7 | Health Science Research Resource Bank of the Japanese Health Sciences Foundation #JCRB1025 | 1,217,989 | 181.73 |
| O | NCI-N87 | ATCC # CRL-5822 ™ | 1,233,479 | 366.10 |
| P | OVCAR8 | NCI 60-cell panel from NCI-DTP | 53,272 | 99.79 |
| Q | OVCAR8-Her2 | NCI 60-cell panel from NCI-DTP, stably transfected with HER2 | 673,300 | 711.87 |
| R | SkBr3 | ATCC # HBT-30 ™ | 1,315,512 | 228.68 |
| S | SKOV3 | ATCC # HTB-77 ™ | 1,377,661 | 600.81 |
| T | ZR75-1 | ATCC # CRL-1500 ™ | 199,132 | 30.32 |

(Results for MKN-45 cells were below detection level)

TABLE 2

HER2 levels vs PLD uptake

Figure 1B:
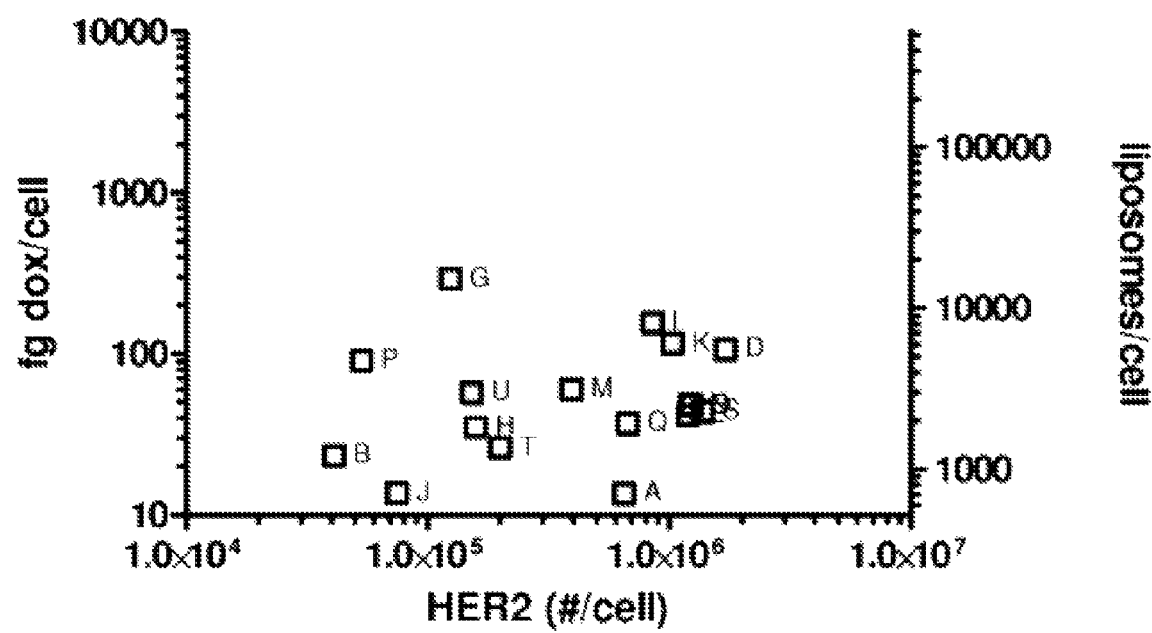
FIG. 1B depicts a graph of the expression of HER2 in multiple cell lines after being treated with 15 μg/ml of untargeted pegylated liposomal dox (UT-PLD) containing doxorubicin (dox) for 2 hr and levels of total cellular doxorubicin internalized as determined using HPLC. The y-axes represent femtograms dox per cell (left) and liposomes per cell (right) and the x-axes represent the number of HER2 receptors per cell (log scale).

| FIG. 1B | Cell Line | Source | HER2 (#/cell) | fg dox/cell |
|---|---|---|---|---|
| A | 4T1-clone-12W7 | ATCC # CRL-2539 ™ | 650,000 | 13.54 |
| B | ADRr | ADR-RES (NCI-DTP) | 40,792 | 23.24 |
| D | BT474-M3 | Noble, Cancer Chemother. Pharmacol. 2009 64: 741-51 | 1,706,601 | 106.60 |
| E | Calu-3 | ATCC # HTB-55 ™ | 1,196,976 | 41.64 |
| G | HeLa | ATCC # CCL-2 ™ | 123,713 | 291.11 |
| H | IGROV1 | NCI 60-cell panel from NCI-DTP | 158,418 | 34.94 |
| I | JIMT-1 | DSMZ # ACC-589 | 850,000 | 155.46 |
| J | MCF7 | ATCC # HTB-22 | 74,745 | 13.57 |
| K | MCF7-c18 | Gift from Dr. Christopher Bentz, Director, Cancer and Developmental Therapeutics Program, Buck Institute for Age Research, UCSF | 1,031,247 | 115.88 |
| M | MDA-MB-453 | ATCC # HBT-131 ™ | 393,441 | 59.97 |
| N | MKN-7 | Health Science Research Resource Bank of the Japanese Health Sciences Foundation #JCRB1025 | 1,217,989 | 48.24 |
| O | NCI-N87 | ATCC # CRL-5822 ™ | 1,233,479 | 47.44 |
| P | OVCAR8 | NCI 60-cell panel from NCI-DTP | 53,272 | 90.53 |
| Q | OVCAR8-Her2 | NCI 60-cell panel from NCI-DTP, stably transfected with HER2 | 673,300 | 37.00 |
| S | SKOV3 | ATCC # HTB-77 ™ | 1,377,661 | 43.83 |
| T | ZR75-1 | ATCC # CRL-1500 ™ | 199,132 | 26.10 |
| U | MKN-45 | DSMZ # ACC-409 | 152,197 | 57.02 |

(Results for AdRr-Her2, HCC1954, and MDA-MB-361 cells were below detection level)

Figure 1C:
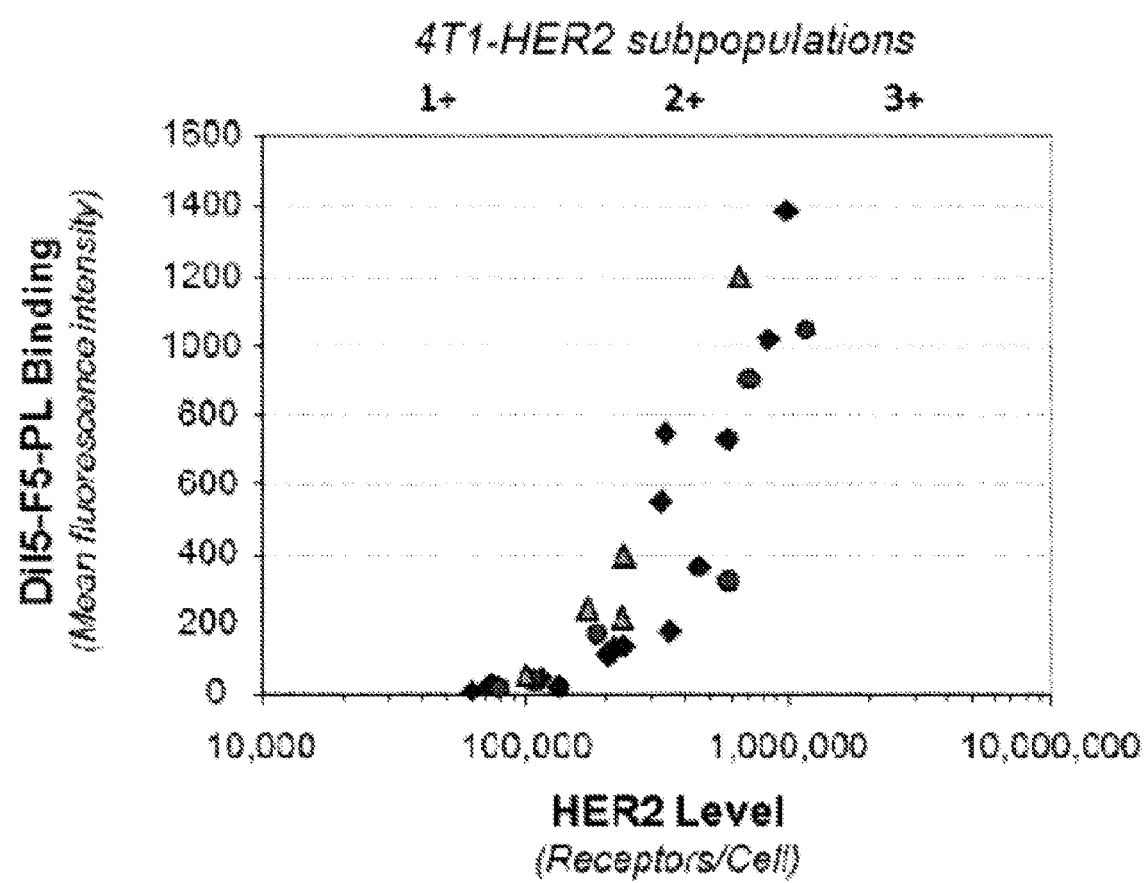
FIG. 1C is a graph depicting the expression of HER2 receptors in Mouse tumor 4T1 cells transfected with human HER2 to generate stable clones with varying levels of expression. Individual clones (represented by triangles, circles, or squares) were treated with F5-targeted liposomes containing a fluorescent marker (DiI5-F5-PL), and total binding/uptake was determined by FACS.
Figure 1D:
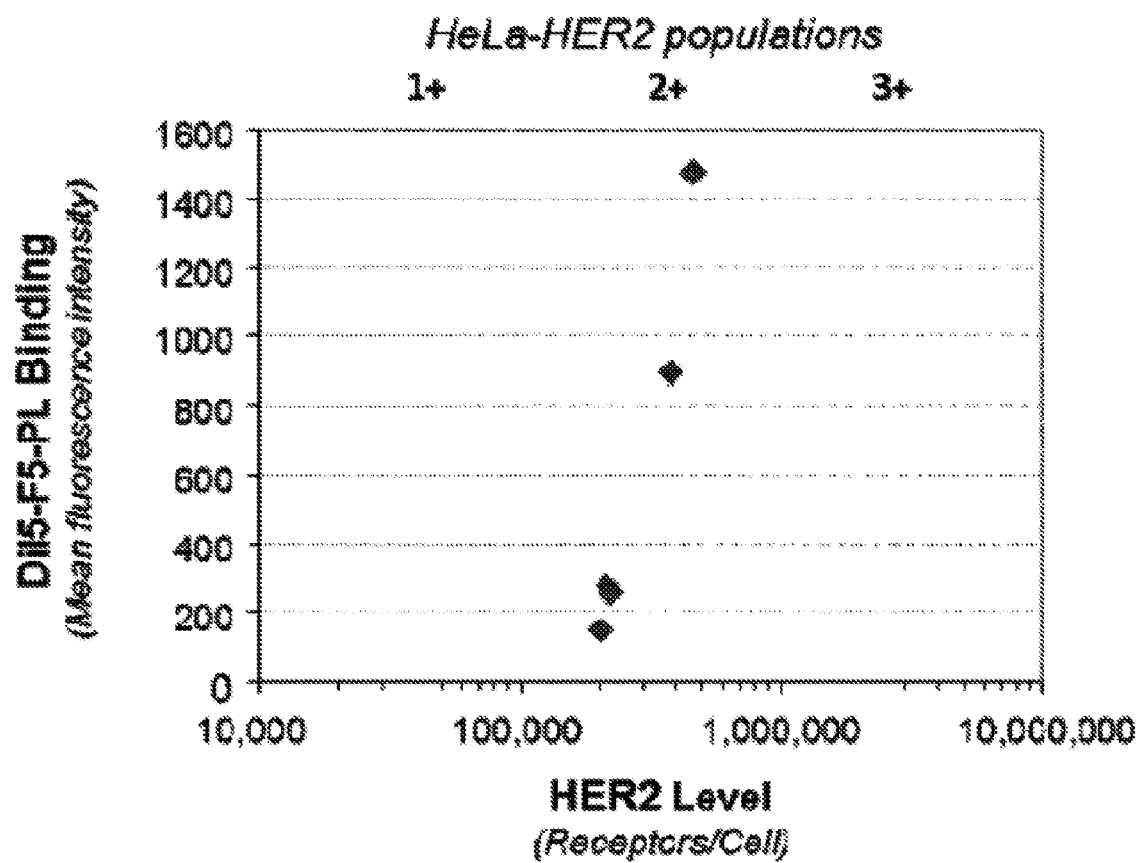
FIG. 1D is a graph depicting the expression of HER2 receptors in endogenously low HER2 expressing HeLa cells transfected with human HER2 to generate stable clones with varying levels of expression. Individual clones (represented by triangles, circles, or squares) were treated with F5-targeted liposomes containing a fluorescent marker (DiI5-F5-PL), and total binding/uptake was determined by FACS.

In order to quantify uptake into the different cell populations, MM-302 was prepared to contain a red-fluorescent carbocyanine tracer DiIC18(5)-DS (Invitrogen D12730—abbreviated DiI5). DiI5 is a lipophilic fluorescent dye that intercalates into the lipid bilayer of the liposome during the extrusion process. 4T1-Her2 cell populations expressing different ranges of human HER2 were incubated with 10 μg/ml fluorescently labeled MM-302 for 3 hrs, washed and incubated for an additional 21 hrs. Cells were harvested, stained for cell surface human HER2 and analyzed for both HER2 levels and liposome binding via flow cytometry. While the 4T1 cell line expresses murine HER2, MM-302 does not bind to the murine receptor. The figure shows that uptake of these liposomes into 4T1 cells was strongly dependent on human HER2 expression (FIG. 1C). Similar results were obtained for populations of the HeLa cell lines expressing different ranges of HER2 (FIG. 1D). These results further demonstrate that MM-302 is highly effective in binding cells with high HER2 levels but has little or no binding to cells with relatively lower HER2 protein expression.

Example 2

Figure 2A:
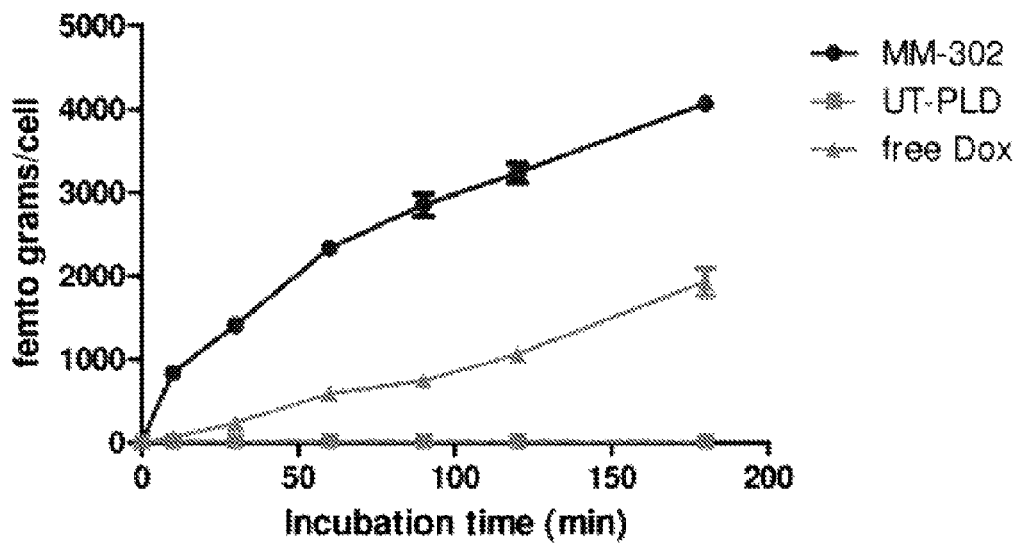
FIG. 2A is a line graph depicting the total cellular doxorubicin quantified by HPLC (y-axis, femtograms/cell) in HER2-overexpressing BT474-M3 cells when treated with 15 μg/ml of MM-302 (circle), PLD (square), and free doxorubicin (triangle) for the indicated times (x-axis, in min.).
Figure 2B:
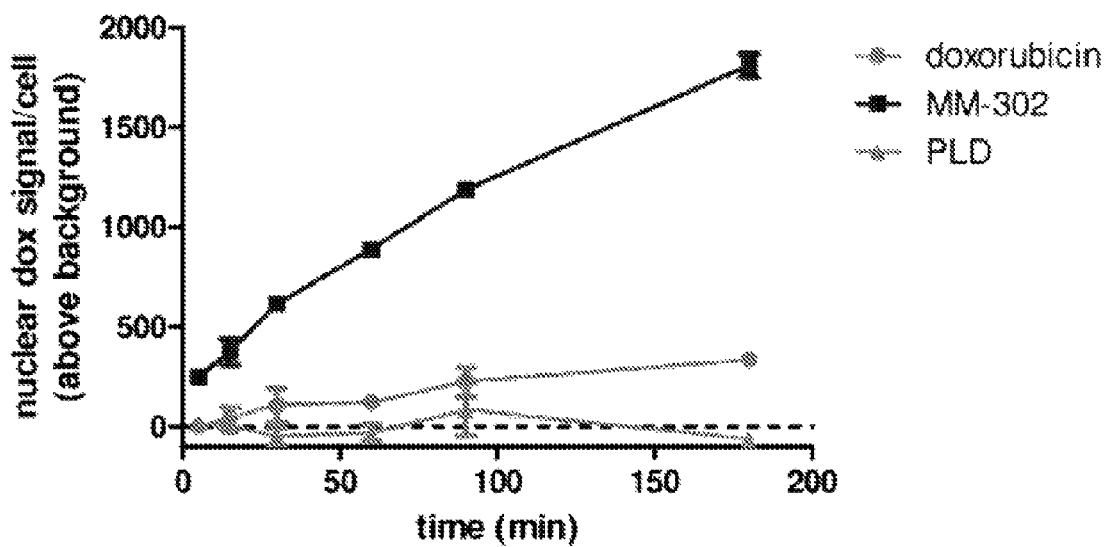
FIG. 2B is a line graph depicting nuclear doxorubicin delivery quantified by high content microscopy (y-axis, signal per cell above background) when treated with 15 μg/ml of MM-302 (square), PLD (triangle), and free doxorubicin (circle) 24 h following the indicated incubation times (x-axis, in min.).

MM-302 is Effectively Internalized into HER2-Overexpressing Tumor Cells and Significantly Inhibits Tumor Growth in a Xenograft Model To determine levels of binding and internalization of MM-302 into HER2 over-expressing tumor cells, BT474-M3 cells ($1.7 \times 10^6$ HER2/cell) were incubated with MM-302, PLD or free doxorubicin at 15 µg/ml for up to 3 h (FIG. 2A). MM-302 was efficiently taken into tumor cells, as evidenced by total cell binding (FIG. 2A) and nuclear doxorubicin accumulation (FIG. 2B). By contrast, the untargeted analogue, PLD, did not show any appreciable accumulation demonstrating the requirement of targeting to effectively deliver liposomal doxorubicin in vitro. As a control, free doxorubicin was shown to freely enter cells and accumulate in the nucleus. Results showed effective binding and internalization of MM-302 (but not PLD) into HER2-overexpressing tumor cells.

Figure 2C:
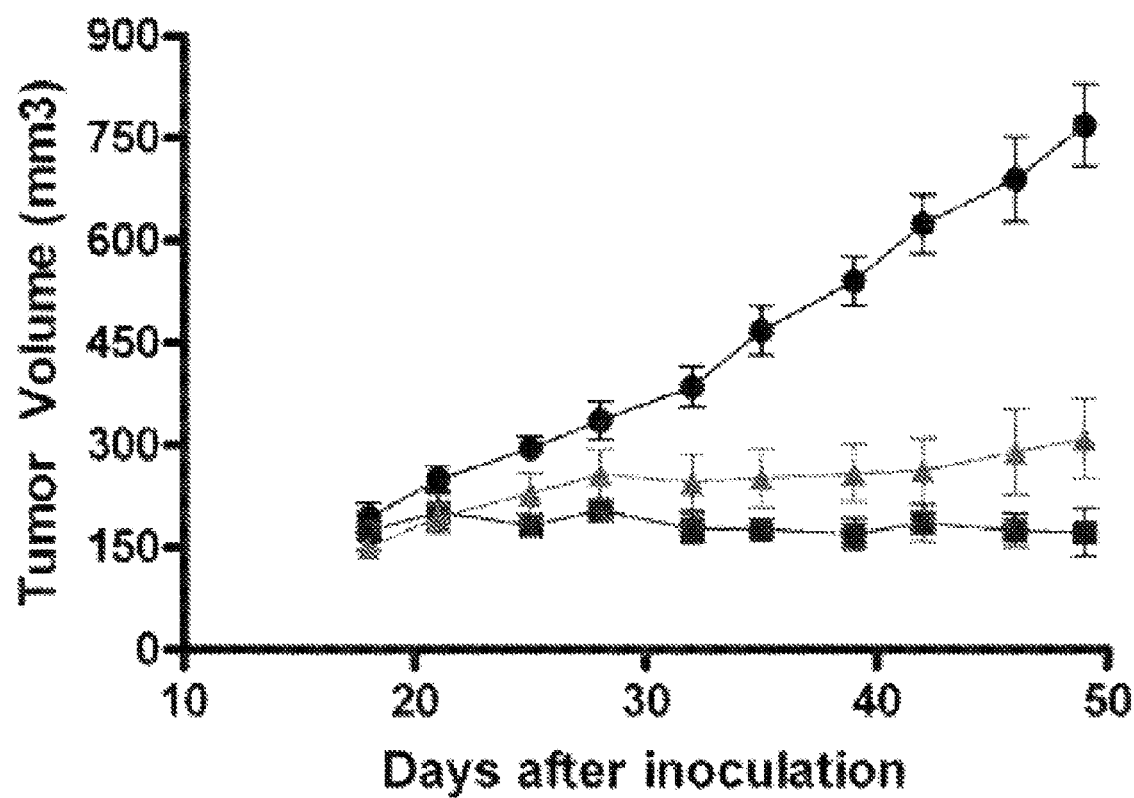
FIG. 2C is a line graph depicting the anti-tumor activity of MM-302 and PLD in a BT474-M3 orthotopic breast cancer model. Both MM-302 (square) and PLD (triangle) significantly inhibited tumor growth compared to control (circle). The y-axis indicates tumor volume in mm$^3$ and the x-axis indicates days after inoculation.
Figure 2D:
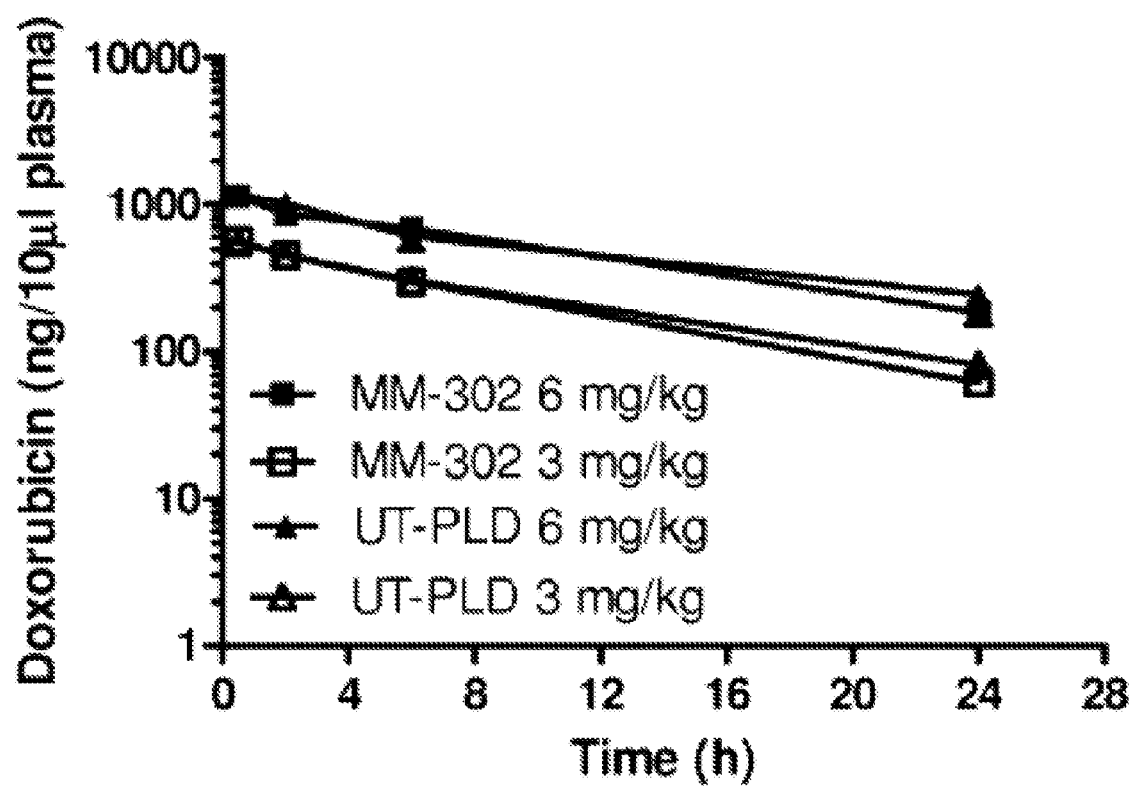
FIG. 2D is a line graph depicting the pharmacokinetics of MM-302 and UT-PLD in BT474-M3 xenografts administered with 3 mg/kg or 6 mg/kg (dox equiv) at q7d. The y-axis is μg/mL dox in plasma and the x-axis is time in hours.

The anti-tumor activity of MM-302 was evaluated in a breast cancer xenograft model. Mice were inoculated with BT474-M3 cells and when the tumor volumes reached an average of 250 mm$^3$, treatment with PBS (control), MM-302 or PLD (both at 6 mg/kg dox equiv.) was started (q7d, n=3 doses). Both MM-302 and PLD significantly inhibited tumor growth relative to control (t-test at day 55; $p<0.0001$). MM-302 resulted in a stronger inhibition of tumor growth relative to PLD (t-test at day 55; $p=0.0310$) (FIG. 2C). At study termination, 3 complete regressions were observed with MM-302 and only 1 with PLD. MM-302 and PLD had similar pharmacokinetic profiles (FIG. 2D) indicating that the improved efficacy was as a result of HER2-targeting, rather than prolonged exposure.

Example 3

Impact of HER2 Levels on MM-302 Uptake in Vivo

Figure 3A:
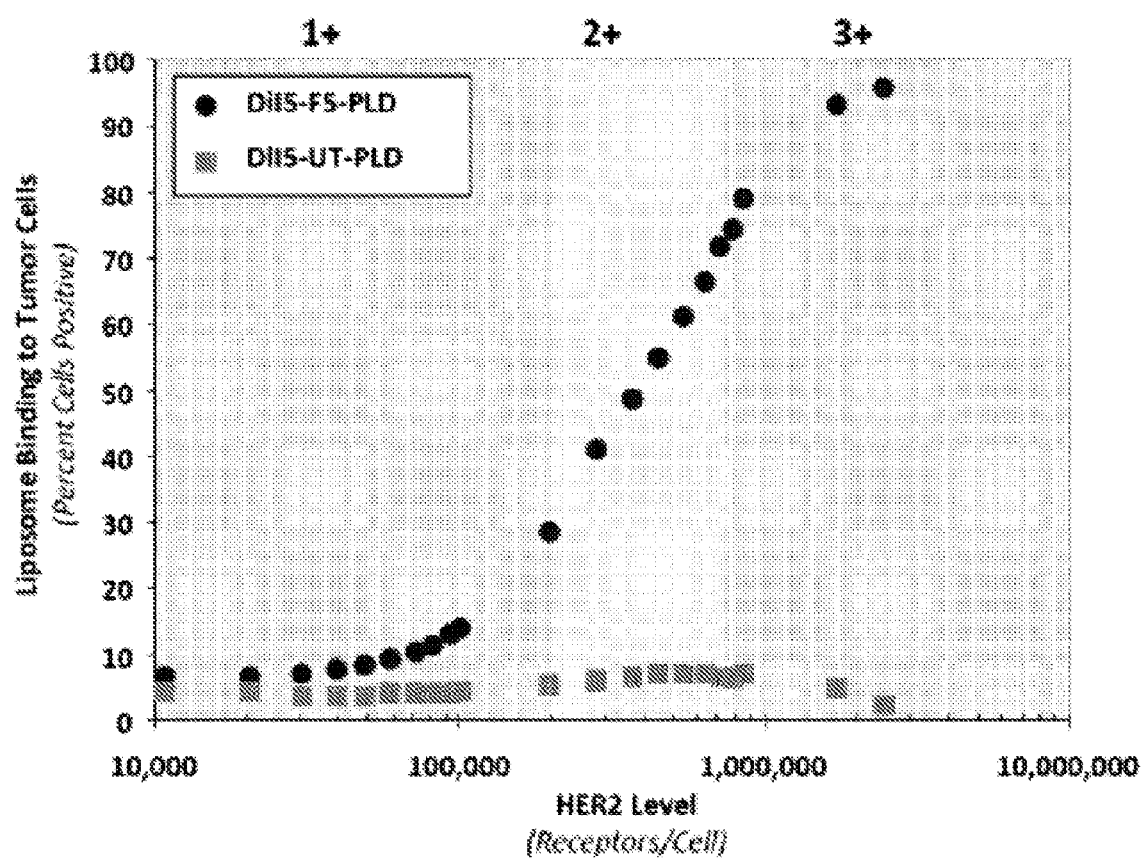
FIG. 3A represents a line graph showing HER2 level (receptors per cell, x-axis) as a function of liposome Di15-labeled MM-302 (Di15-F5-PLD) or UT-PLD (Di15-UT-PLD) binding to BT474-M3 xenograft tumor cells (percent cells positive, y-axis).

Experiments were conducted to demonstrate HER2-mediated uptake of MM-302 into target tumor cells from xenograft models compared with untargeted liposomal doxorubicin. Mice bearing BT474-M3 xenograft tumors in the mammary fat pad were injected with Di15-labeled MM-302 (Di15-F5-PLD) or UT-PLD (Di15-UT-PL). A tumor single cell suspension was prepared and stained with FITC-HER2 antibodies. Di15-positive-HER2-positive cells were determined by FACS. A distinct population of cells with elevated doxorubicin levels was identified, indicating that liposomes had not just been deposited in the tumor interstitial space, but had been taken up into the cells themselves (FIG. 3A). This was particularly evident in cell samples derived from tumors treated with HER2-targeted liposomes. The percentage of cells with elevated liposome content began to rise in cell subsets expressing on average 100,000 and 200,000 HER2 receptors per cell. Untargeted liposomes did not show any preferential uptake into HER2 positive cells. These results demonstrate that MM-302 uptake in tumor cells in vivo is HER2-dependent and further support a level of at least 100,000-200,000 HER2 receptors per cell necessary to allow significant binding and internalization of MM-302.

Figure 3B:
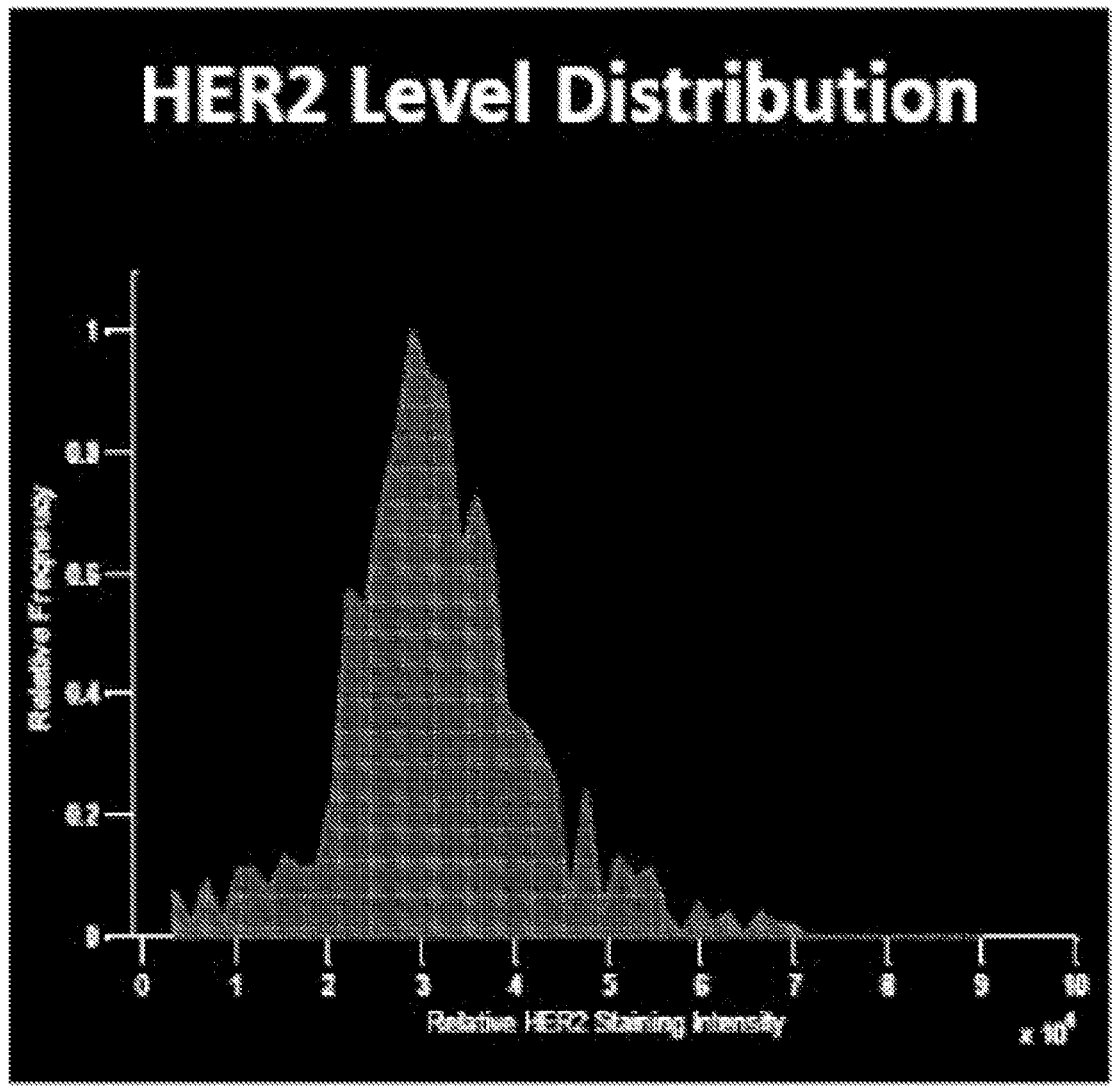
FIG. 3B represents a line graph demonstrating the heterogeneity of HER2 expression on a single cell basis as measured in tumor tissue sections.

The distribution of HER2 membrane intensity was determined on a single-cell basis in full tissue sections and is shown in FIG. 3B, representing the variability of expression in the tissue.

Example 4

Human Cardiomyocytes do not Express Sufficient HER2 Levels to Actively Take up MM-302

Human cardiomyocytes have been reported to express low levels of HER2, and therefore were thought to have potential for MM-302 uptake. ESCd and iPSd human cardiomyocytes were obtained to study the effect of MM-302 on human cardiac cells in vitro. HER2 receptor levels on cardiomyocytes were determined by qFACS to be approximately 70,000 and 200,000 receptors per cell in human ESCd and iPSd cardiomyocytes, respectively. These results are consistent with the reported low HER2 expression in human cardiac tissue (Fuchs et al., Breast Cancer Res Treat. 2003; 82:23-8).

HER2 expression levels on normal and diseased human heart tissue were measured via quantitative immunohistochemistry. A human heart Tissue Microarray (TMA) was stained for HER2 and DAPI and the (Mean HER2 intensity)/core was quantified with Definiens® software. A cell pellet array with cell lines at different HER2 expression levels was stained as above and the (Mean HER2 intensity)/core was quantified and plotted against the correspondent LOG (HER2 receptor #) to generate a standard. Based on the generated standard, the average HER2 receptor #/core for the different human heart TMA cores was interpolated (Table 3).

TABLE 3

Interpolated HER2 Receptor Number

| ID | Pathology Diagnosis | HER2 # |
|---|---|---|
| 1 | Chronic rheumatic valvular disease with calcification | 40,000 |
| 2-pt1 | Chronic rheumatic valvular disease | 38,000 |
| 2-pt2 | Chronic rheumatic valvular disease | 38,000 |
| 2-pt3 | Chronic rheumatic valvular disease | 47,000 |
| 2-pt4 | Chronic rheumatic valvular disease | 47,000 |
| 2-pt5 | Chronic rheumatic valvular disease | 39,000 |
| 2-pt6 | Chronic rheumatic valvular disease | 38,000 |
| 2-pt7 | Chronic rheumatic valvular disease | 42,000 |
| 2-pt8 | Chronic rheumatic valvular disease | 42,000 |
| 2-pt9 | Chronic rheumatic valvular disease | 41,000 |
| 3 | Hepatocellular carcinoma embolus of cardiac atrium | 44,000 |
| 4 | Hypertrophic cardiomyopathy | 38,000 |
| 5 | Normal great arteries tissue | 37,000 |
| 6 | Normal cardiac atrium tissue | 37,000 |
| 7 | Normal myocardial tissue (focal mild hypertrophy) | 38,000 |
| 8 | Normal auricle of heart tissue | 48,000 |
| 9 | Normal myocardial tissue (mild hypertrophy) | 38,000 |
| 10 | Normal myocardial tissue | 38,000 |

Figure 4A:
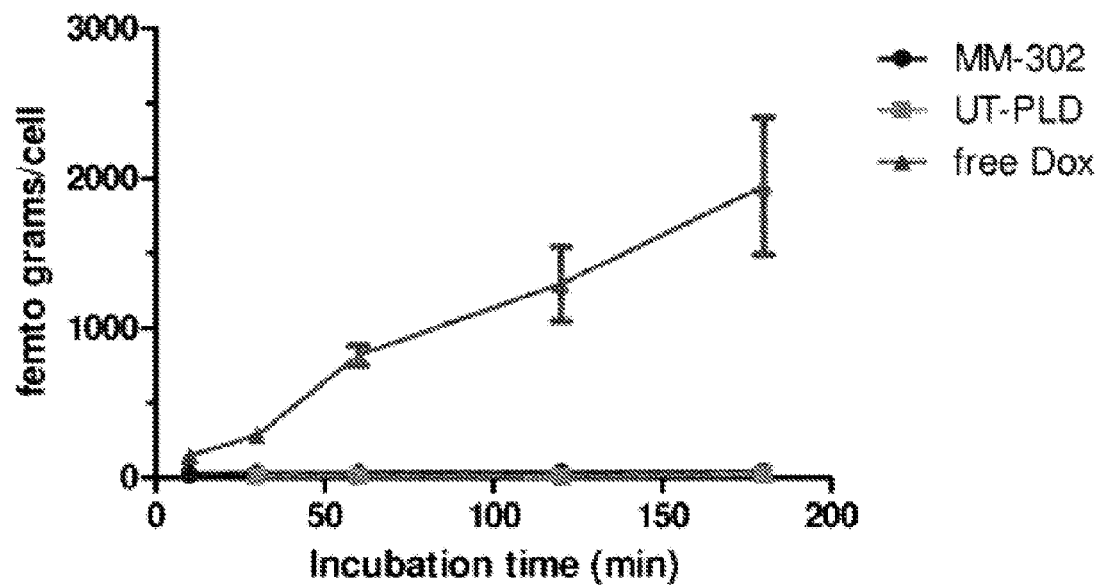
FIG. 4A depicts a line graph illustrating the uptake of MM-302 (circle), PLD (square) and doxorubicin (triangle) in human embryonic stem cell-derived (ESCd) cardiomyocytes. Total cellular doxorubicin was quantified by HPLC. The y-axes represents uptake in femtograms/cell and the x-axes represent incubation time in min.
Figure 4B:
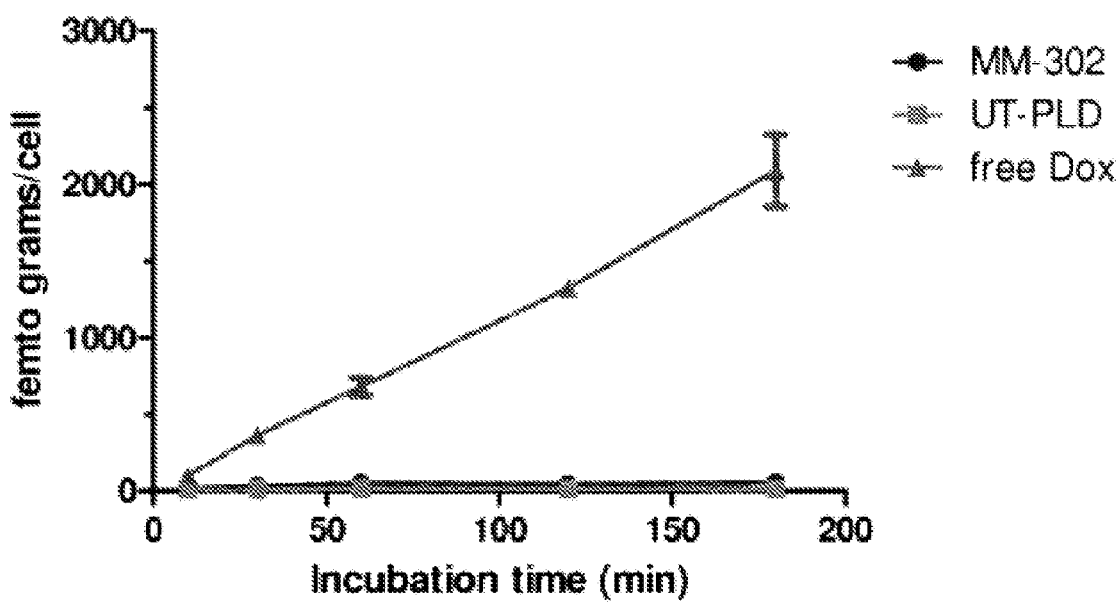
FIG. 4B depicts a line graph illustrating the uptake of MM-302 (circle), PLD (square) and doxorubicin (triangle) in human induced pluripotent stem cell-derived (iPSd) cardiomyocytes. Total cellular doxorubicin was quantified by HPLC. The y-axes represents uptake in femtograms/cell and the x-axes represent incubation time in min.

To determine if the level of HER2 expression on cardiomyocytes is sufficient to induce uptake of MM-302, total cellular doxorubicin was quantified by HPLC following treatment of ESCd (FIG. 4A) and iPSd (FIG. 4B) cardiomyocytes. Cardiomyocytes (and cancer cells) treated with free doxorubicin result in doxorubicin accumulation in all cells. Treatment with PLD did not result in an increase in doxorubicin delivery in either cardiomyocyte cell type. In contrast to HER2-overexpressing cancer cells, the HER2 expression level on cardiomyocytes was not sufficient to promote active uptake of MM-302. Taken together, these results demonstrate delivery of doxorubicin via MM-302 does not enhance doxorubicin exposure to low level HER2 expressing non-target cells such as cardiomyocytes as compared to PLD.

Example 5

Figure 4C:
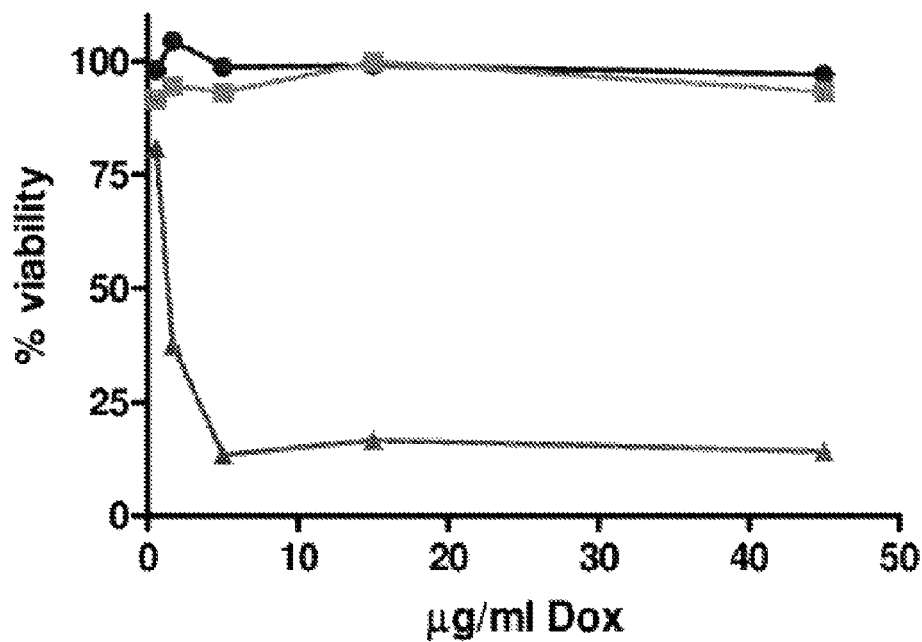
FIG. 4C depicts a line graph illustrating the cell viability of ESCd cardiomyocytes after treatment for 3 h with drug (free doxorubicin (circle), PLD (square) or MM-302 (triangle)) at the indicated concentrations and incubated for an additional 24 h with fresh media. The y-axis represents cell viability as % compared to control and the x-axis represents concentration in μg/ml.
Figure 4D:
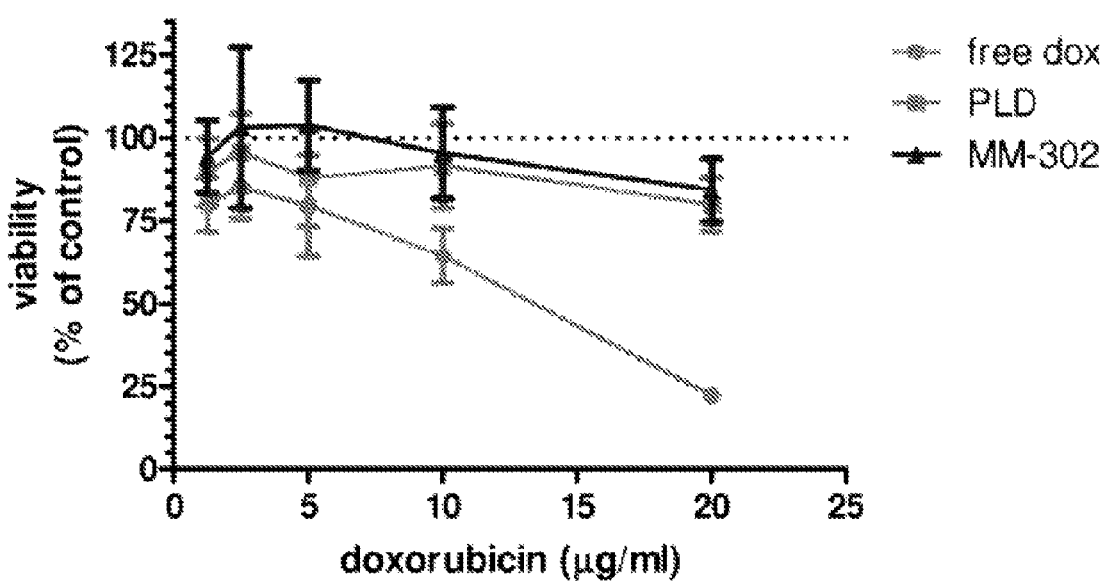
FIG. 4D depicts a line graph illustrating the cell viability of human induced pluripotent stem cell-derived (iPSd) cardiomyocytes after treatment for 24 hours with drug (free doxorubicin (circle), PLD (square) or MM-302 (triangle)) at the indicated concentrations and incubated for an additional 24 h with fresh media. The y-axis represents cell viability as % compared to control and the x-axis represents concentration in μg/ml. The supernatant was collected and a PrestoBlue® cell viability assay was performed on the remaining cells.
Figure 4E:
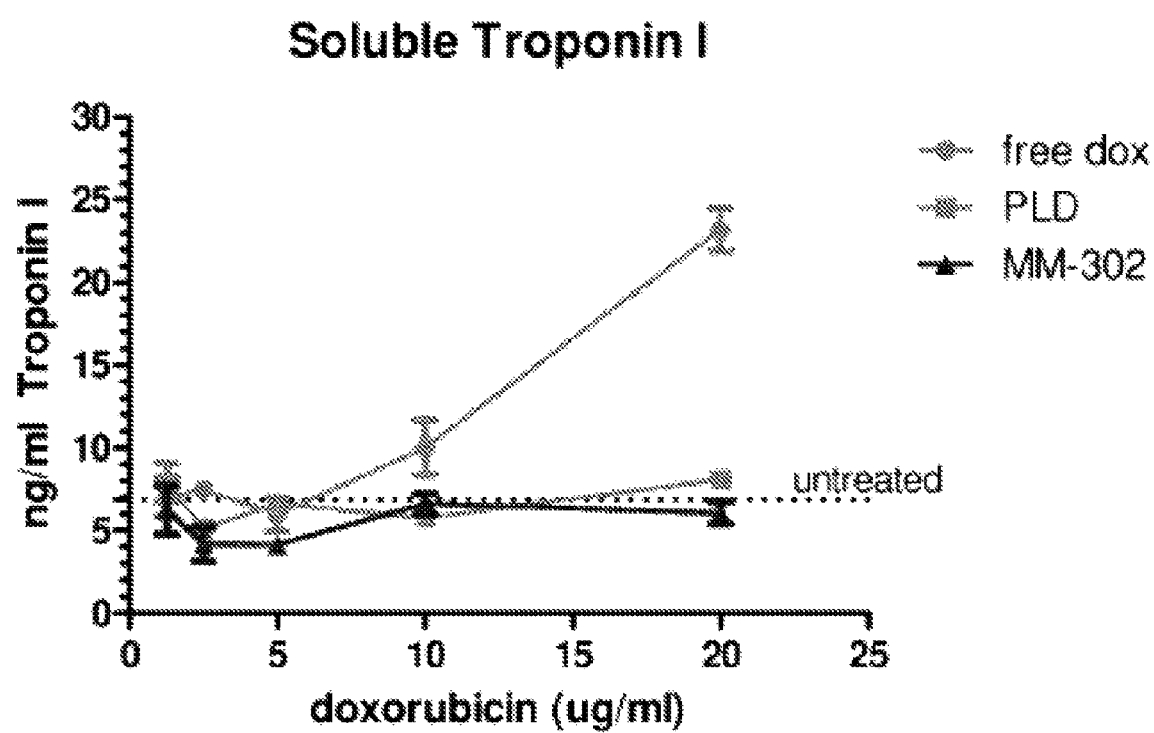
FIG. 4E depicts expression of human Troponin I using an ELISA assay performed on the supernatant collected in (FIG. 4D). The untreated line (dotted line) represents the value of soluble Troponin I detectable in untreated wells. All values are normalized against dilutions of a supplied standard.

MM-302 does not Reduce Human Cardiomyocyte Viability or Stimulate Apoptotic Responses Exposure to low levels of doxorubicin can be cytotoxic. To determine if treatment with MM-302 or PLD affected cardiomyocyte viability, ESCd cardiomyocytes were incubated with free dox, PLD or MM-302 for 3 h at the indicated concentration followed by washing and incubation in fresh media for 24 h. Treatment with free doxorubicin resulted in a loss of viability at concentrations as low as 0.2 µg/ml (FIG. 4C). Conversely, treatment with MM-302 and PLD did not lead to reductions in viability at any concentration tested, including super-therapeutic concentrations up to 45 µg/ml. To further test whether treatment with MM-302 or PLD affected cardiomyocyte viability, iPSd cardiomyocytes were treated with the indicated concentration of free doxorubicin, PLD or MM-302 for 24 hours. Treatment with doxorubicin resulted in a marked decrease in viability as compared to treatment with PLD and MM-302 (FIG. 4D). The presence of elevated levels of cardiac troponins is a clinical indicator of cardiac damage. The supernatant from the iPSd cardiomyocytes in (D) was analyzed for levels of troponin I. As shown in FIG. 4E, doxorubicin treatment resulted in a marked increase of Troponin I compared to treatment with PLD or MM-302. These results demonstrate that ESCd and iPSd cardiomyocytes are sensitive to doxorubicin, and that treatment with MM-302 and PLD does not provide sufficient doxorubicin exposure to affect cardiomyocyte viability.

Exposure of cells to low levels of doxorubicin may induce subtle cellular changes not revealed by cell viability measurements, including DNA damage, cell stress and incipient apoptosis. Following treatment with MM-302, PLD and free doxorubicin, cardiomyocytes were stained for proteins in each of these response pathways and imaged using high-content microscopy. Single-cell data were generated by analyzing the resulting images using ImageRail.

Figure 5A:
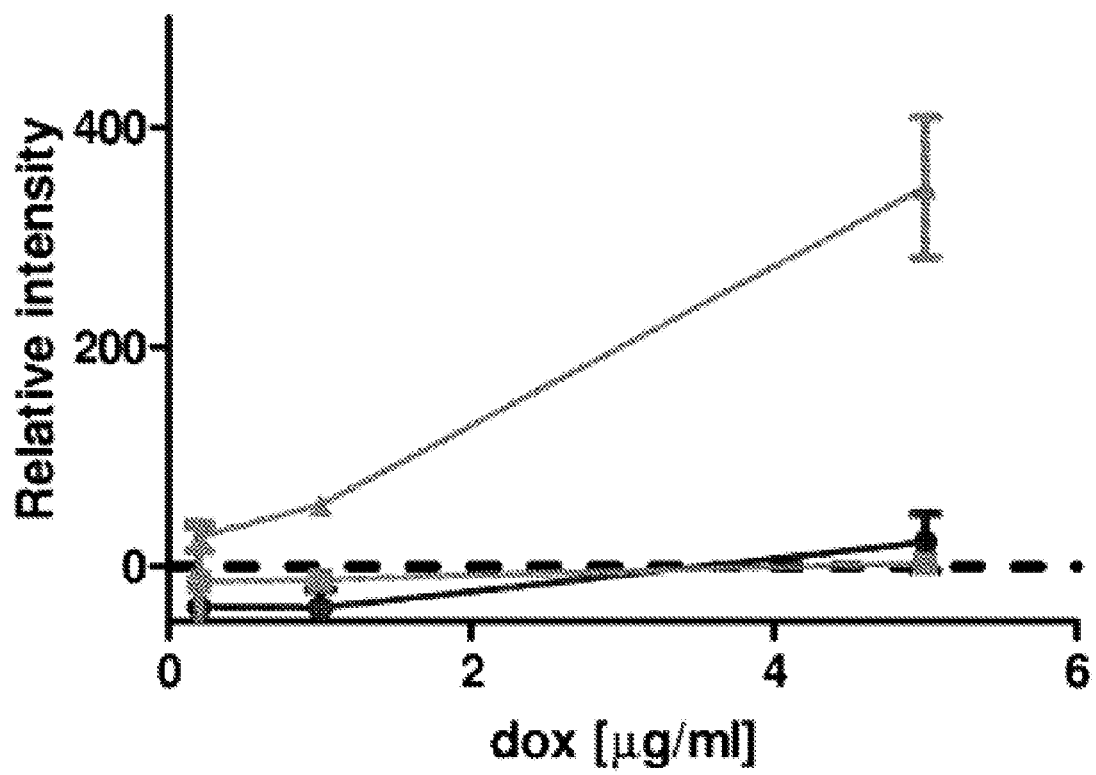
FIG. 5A depicts a line graph representing expression the DNA damage marker gamma-H2AX in ESCd cardiomyocytes after treatment for 3 h with MM-302 (circle), PLD (square), and free doxorubicin (triangle) at the indicated concentrations and then incubated for an additional 24 h with fresh media. Single cell intensity for each stain was quantified and represented as the mean relative intensity of individual cells.

In response to double-stranded DNA damage, histone H2AX becomes phosphorylated, forming gamma-H2AX. Treatment of cardiomyocytes with free doxorubicin resulted in a dose-dependent increase in nuclear gamma-H2AX (FIG. 5A). However, treatment with MM-302 and PLD did not increase nuclear gamma-H2AX signal at any concentration tested, indicating that liposomal encapsulation prevented DNA damage to cardiomyocytes in vitro.

Figure 5B:
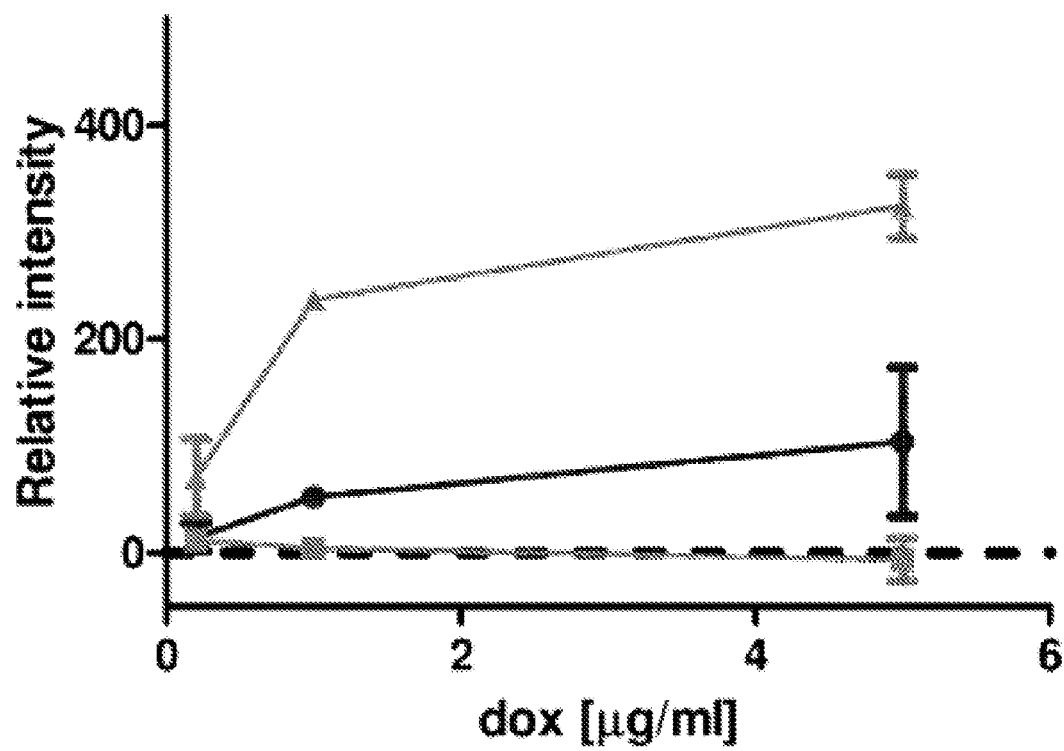
FIG. 5B depicts a line graph representing expression of the cell stress protein phospho-p53 in ESCd cardiomyocytes after treatment for 3 h with MM-302 (circle), PLD (square), and free doxorubicin (triangle) at the indicated concentrations and then incubated for an additional 24 h with fresh media. Single cell intensity for each stain was quantified and represented as the mean relative intensity of individual cells.
Figure 5C:
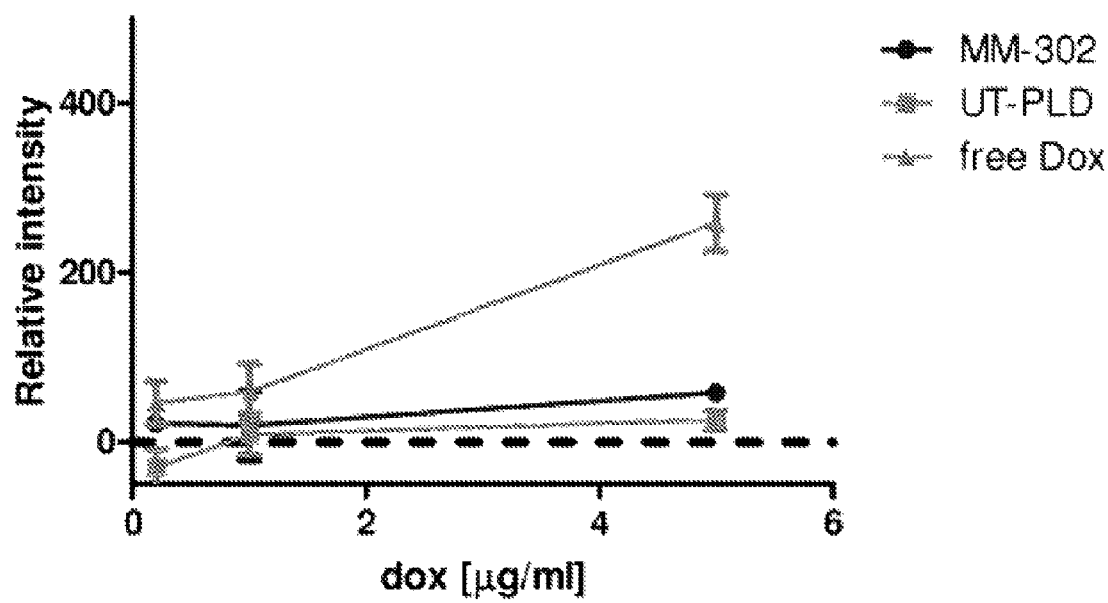
FIG. 5C depicts a line graph representing expression of the cell stress protein phospho-HSP27 in ESCd cardiomyocytes after treatment for 3 h with MM-302 (circle), PLD (square), and free doxorubicin (triangle) at the indicated concentrations and then incubated for an additional 24 h with fresh media. Single cell intensity for each stain was quantified and represented as the mean relative intensity of individual cells.

In response to cellular stress, HSP27 and p53 can be phosphorylated, leading to cell cycle arrest, followed by DNA repair or apoptosis depending on the extent of injury. Cardiac cells exposed to free doxorubicin demonstrate a dose-dependent increase in phospho-HSP27 and phospho-p53 indicating an induction of cellular stress following treatment (FIGS. 5B and 5C). However, an increase in phospho-HSP27 was not observed in cells treated with either MM-302 or PLD regardless of concentration. In most cases, there did not appear to be an effect on phospho-p53 in cells treated with MM-302 or PLD, with the exception of a slight increase in phospho-p53 following treatment with 5.0 µg/ml of MM-302. However, treatment at this and higher concentrations did not result in increased cell death.

Figure 5D:
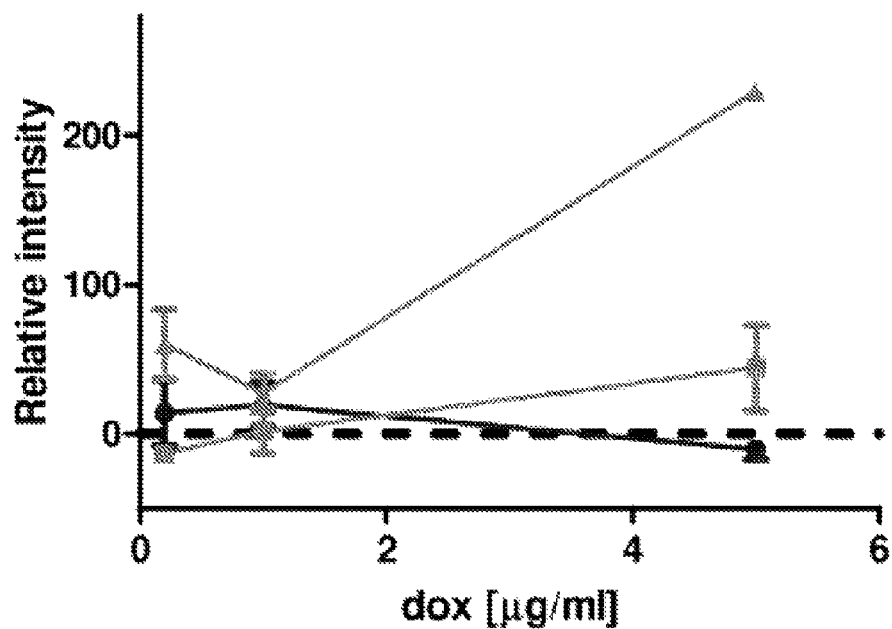
FIG. 5D depicts a line graph representing expression of the cleaved form of the apoptosis protein PARP (cPARP) in ESCd cardiomyocytes after treatment for 3 h with MM-302 (circle), PLD (square), and free doxorubicin (triangle) at the indicated concentrations and then incubated for an additional 24 h with fresh media. Single cell intensity for each stain was quantified and represented as the mean relative intensity of individual cells.

In cases of severe DNA damage and cell stress, the cell may initiate the apoptotic pathway including activation of a caspase cascade, ultimately resulting in the cleavage of the DNA repair protein PARP. Treatment with 5.0 µg/ml of free doxorubicin led to an increase in nuclear cleaved PARP (cPARP) (FIG. 5D), correlating with the observed increase in cell death. However, treatment with MM-302 or PLD did not result in increased nuclear cPARP suggesting that treatment under these conditions is not sufficient to induce apoptosis.

Example 6

Impacts of HER2-Targeted Agents on Intracellular Signaling in Cardiomyocytes

The concurrent use of doxorubicin and trastuzumab is contraindicated due to an unacceptably high incidence of cardiac events observed in patients treated with the combination. The mechanism of action for the cardiotoxicity associated with this combination is believed to be the simultaneous induction of cellular stress by doxorubicin and by trastuzumab-mediated inhibition of HER2 signaling pathways that is necessary to respond to the cellular stress induced by doxorubicin.

Figure 6A:
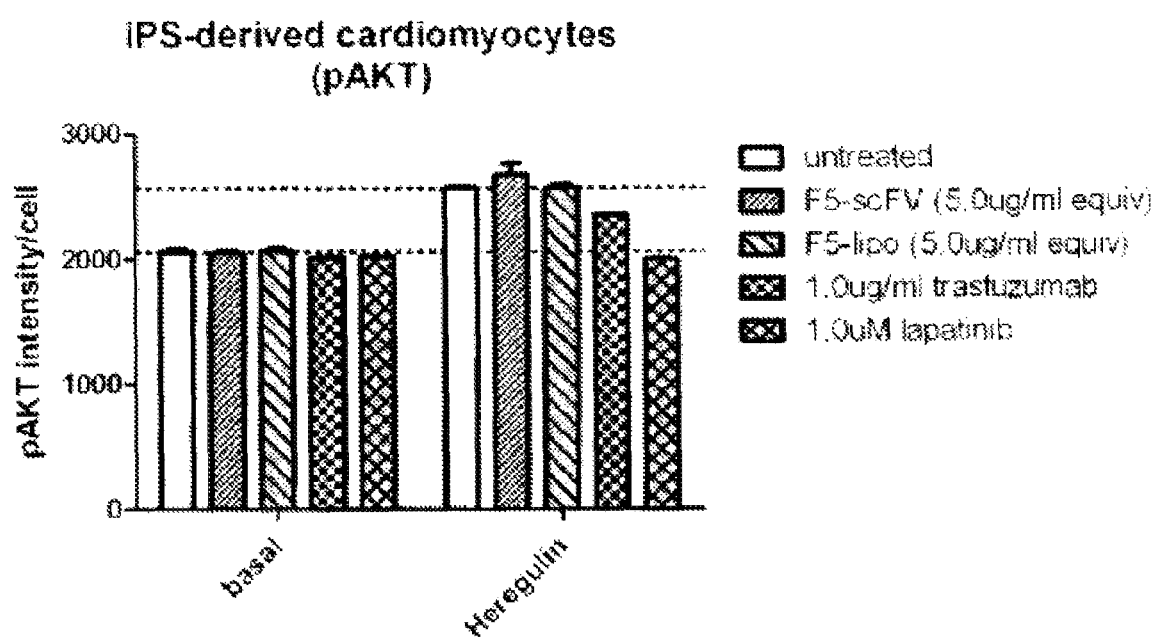
FIG. 6A depicts a bar graph illustrating the effects of F5 scFv alone, F5 scFv bound to empty (i.e. without encapsulated dox) liposomes ("F5 lipo"—liposomes equivalent to MM-302 but not containing doxorubicin), Herceptin® (trastuzumab) and lapatinib on basal and heregulin stimulated pAKT levels in iPS-derived human cardiomyocytes.
Figure 6B:
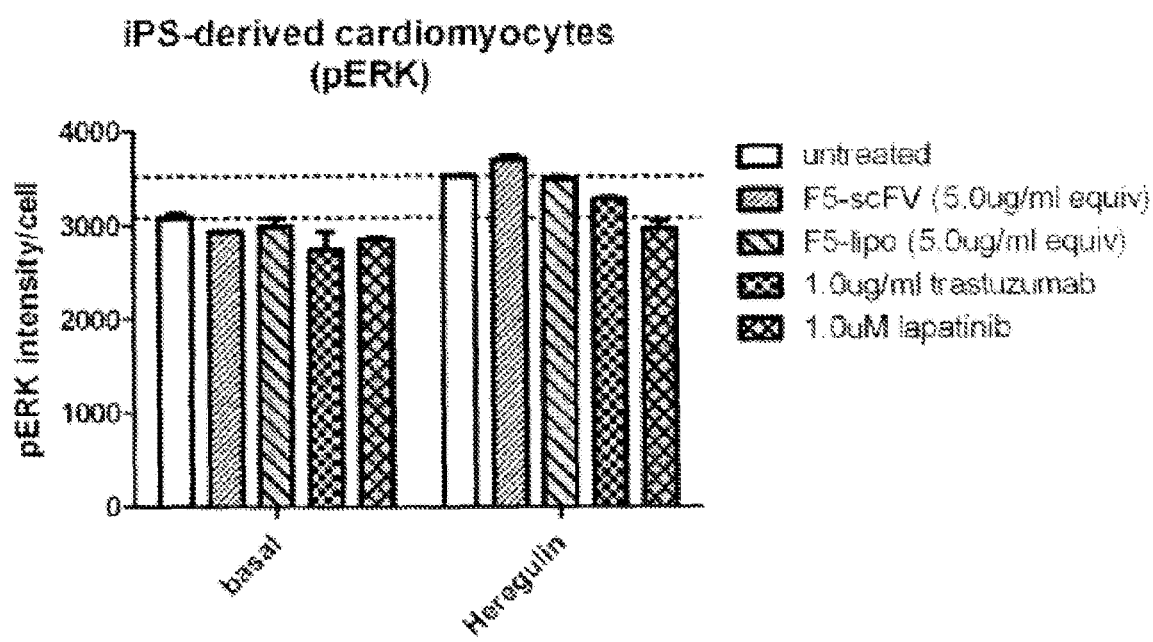
FIG. 6B depicts a bar graph illustrating the effects of F5 scFv alone, F5 scFv bound to empty (i.e. without encapsulated dox) liposomes ("F5 lipo"—liposomes equivalent to MM-302 but not containing doxorubicin), Herceptin® (trastuzumab) and lapatinib on basal and heregulin stimulated pERK levels in iPS-derived human cardiomyocytes.

To determine if pretreatment with MM-302 alters HER2-mediated signaling (an essential pathway in cardiomyocytes), iPDd cardiomyocytes were pretreated for 24 hours with trastuzumab, lapatinib (a small molecule HER2 tyrosine kinase inhibitor), or the MM-302 antibody (F5-scFv) and an empty liposome identical to MM-302 except that it does not contain doxorubicin) (F5-lipo). After stimulation with 10 nM (FIG. 6A) and 5 nM (FIG. 6B) of heregulin (HRG) for 10 min, the levels of phospho-AKT (pAKT, FIG. 6A) and phospho-ERK (pERK, FIG. 6B) were measured by high content microscopy as described above. Pretreatment with trastuzumab for 24 h resulted in a reduction in HRG-mediated phosphorylation of both proteins. Pretreatment with lapatinib led to a reduction in basal phosphorylation of AKT and ERK as well as a complete inhibition of HRG-induced phosphorylation of these proteins. Pre-treatment F5-lipo did not inhibit HRG-induced phosphorylation of AKT or ERK. These results suggest that, despite targeting HER2, MM-302 does not inhibit ligand-induced phospho-AKT and phospho-ERK signaling in cardiomyocytes, leaving these critical signaling pathways functional.

These results also show that trastuzumab and lapatinib have a significantly greater negative impact on this signaling pathway in cardiomyocytes than do F5 scFv or F5 lipo. This in turn is an indication that the anti-HER2 antibody component of MM-302 is less cardiotoxic than the anti-HER2 antibody trastuzumab. The results show that F5, either alone or linked to the exterior of an MM-302 liposome, does not interfere with heregulin (ligand)-stimulated HER2/HER3 heterodimer-mediated signaling in cardiomyocytes which is an essential intracellular signaling modality, inhibition of which is believed to be a key mechanism mediating trastuzumab-induced cardiotoxicity.

Example 7

Figure 7A:
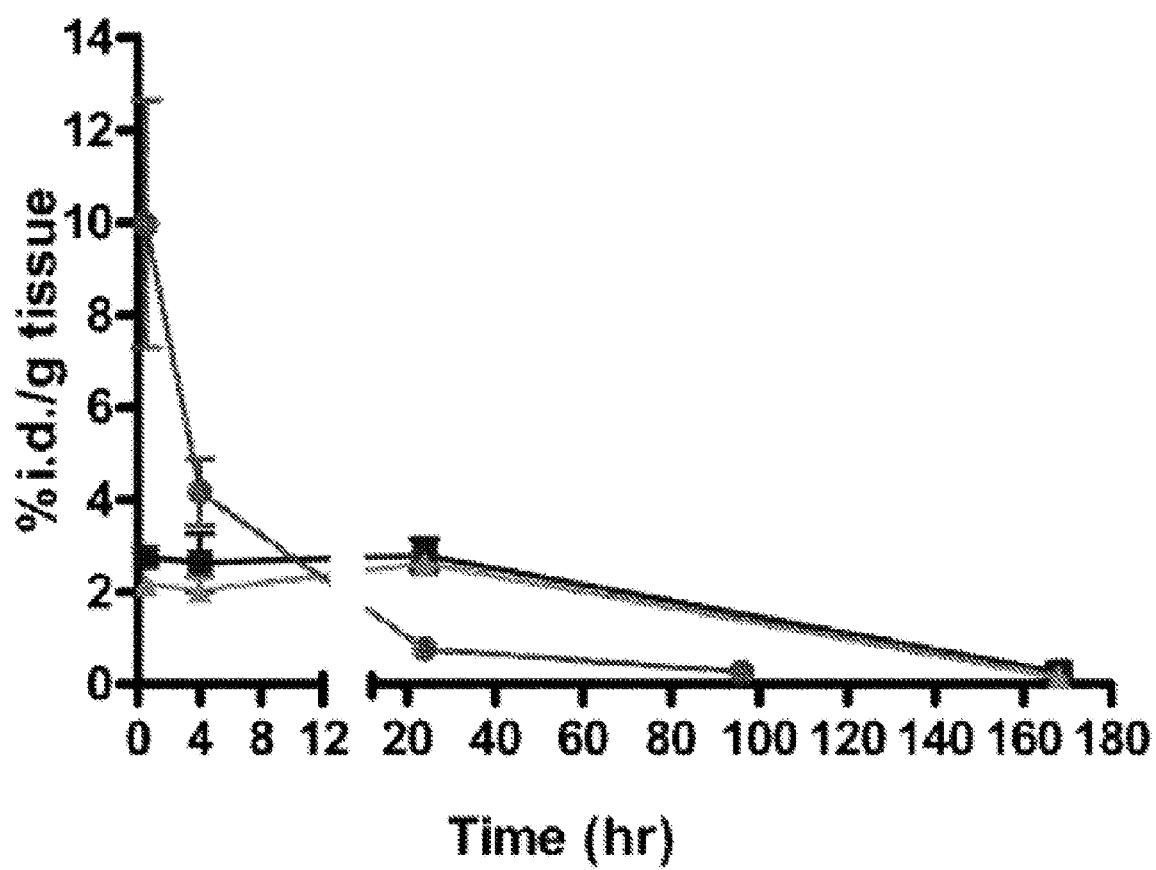
FIG. 7A is a line graph illustrating the biodistribution and accumulation of doxorubicin in heart tissue after administration of MM-302 (square), PLD (triangle) and free doxorubicin (circle) in NCI-N87 tumor bearing mice (n=4/time point/group).
Figure 7B:
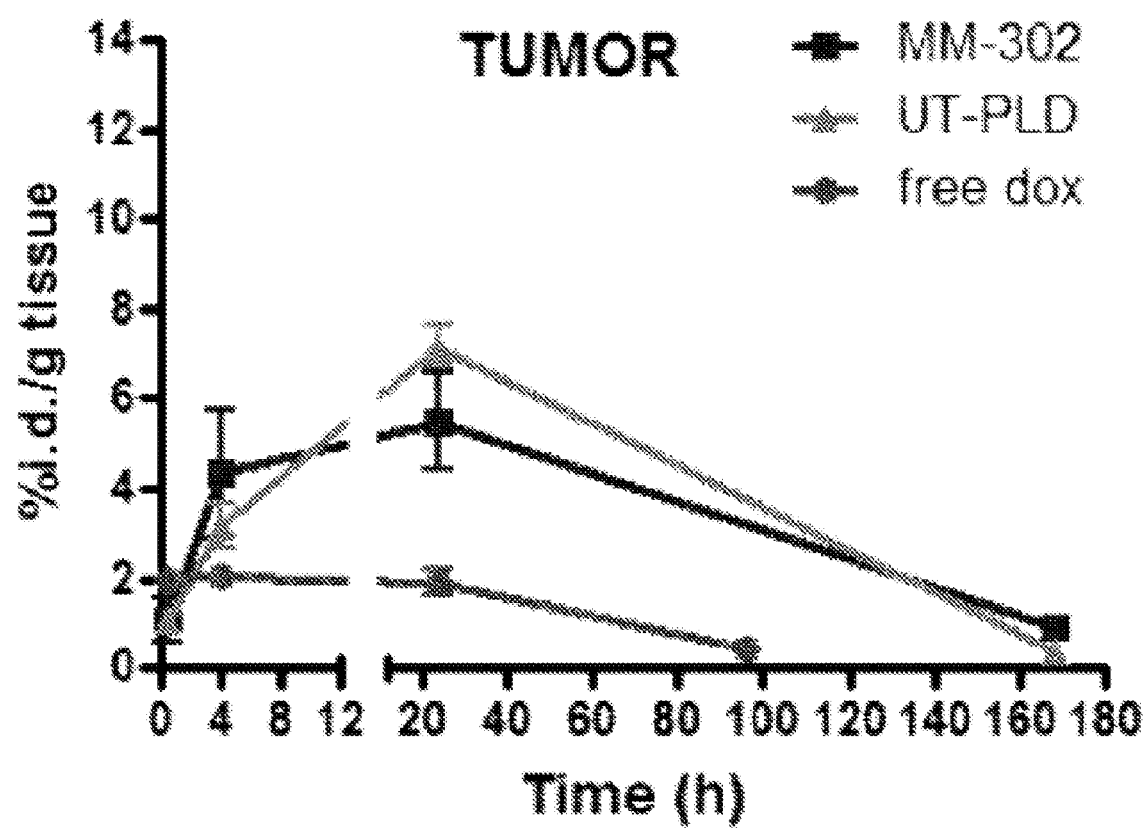
FIG. 7B is a line graph illustrating the biodistribution and accumulation of doxorubicin in tumor tissue after administration of MM-302 (square), PLD (triangle) and free doxorubicin (circle) in NCI-N87 tumor bearing mice (n=4/time point/group).
Figure 7C:
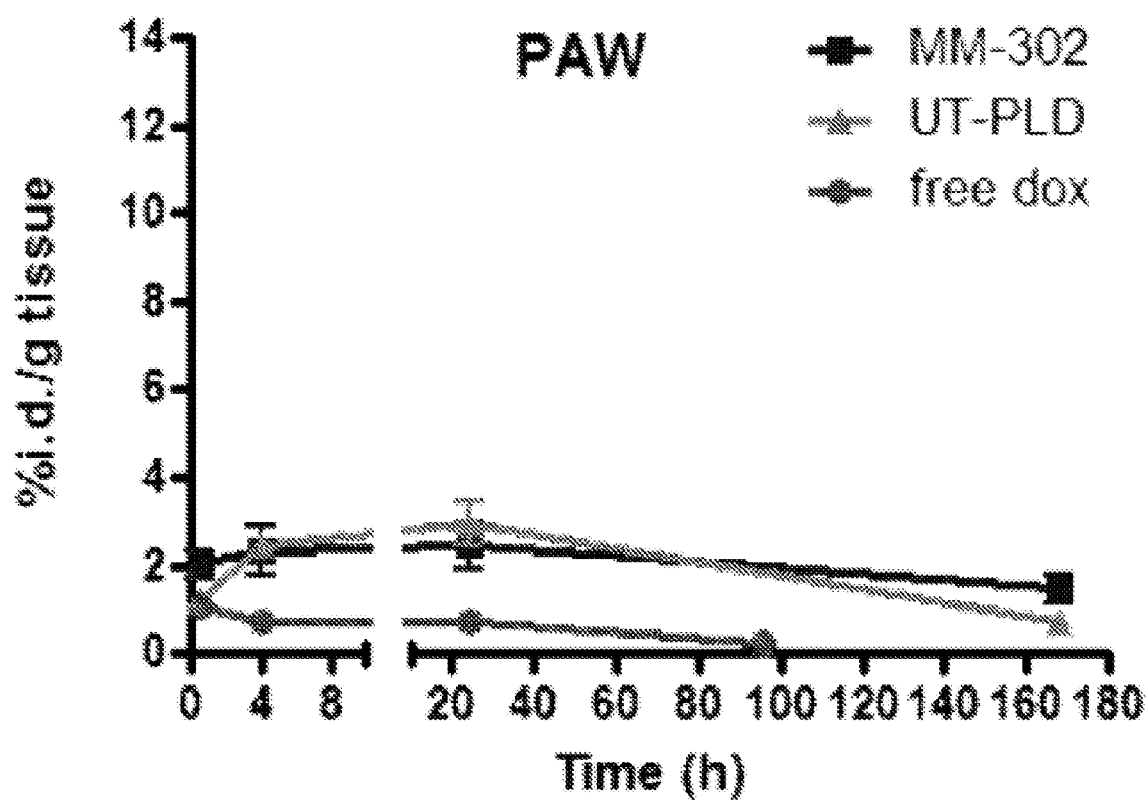
FIG. 7C is a line graph illustrating the biodistribution and accumulation of doxorubicin in paw tissue after administration of MM-302 (square), PLD (triangle) and free doxorubicin (circle) in NCI-N87 tumor bearing mice (n=4/time point/group).

MM-302 has a Lower Accumulation in Mouse Heart Tissue Compared to Free Doxorubicin Liposome targeting with a highly specific antibody fragment such as F5 generally does not alter the total tissue deposition of liposomes, but rather alters their microdistribution following extravasation. The macro-level biodistributions of MM-302 (square), PLD (UT-PLD, triangle) and doxorubicin (free dox, circle) were compared in mouse heart tissue (FIG. 7A), human xenograft tumor tissue (FIG. 7B) and paw tissue (FIG. 7C) in NCI-N87 tumor bearing mice inoculated as described above. Mice (n=4/time point/group) were injected i.v. with MM-302, PLD, or free doxorubicin (all at 3 mg/kg dox equiv.) and hearts were collected at 0.5, 4, 24, and 96 h (for dox) or 168 h (for MM-302 and PLD) post injection and doxorubicin quantified by HPLC (FIG. 7A). Injection of free doxorubicin resulted in a high peak exposure in the heart at 0.5 h (10% of injected dose (i.d.)/g tissue) compared to the two liposomal formulations. The clearance of doxorubicin from the heart tissue after free doxorubicin injection was faster compared to MM-302 and PLD and at 24 h the amount of detected doxorubicin (0.77% of i.d./g tissue) was close to background. Both MM-302 and PLD had a sustained accumulation profile that peaked at 24 h (2.8% and 2.6% for MM-302 and PLD, respectively) while values returned to background at 168 h. These results are in a range similar to that of previously reported data on the heart biodistribution of other PLD formulations. No significant differences were observed between the heart biodistribution of MM-302 and PLD.

Example 8

Figure 7D:
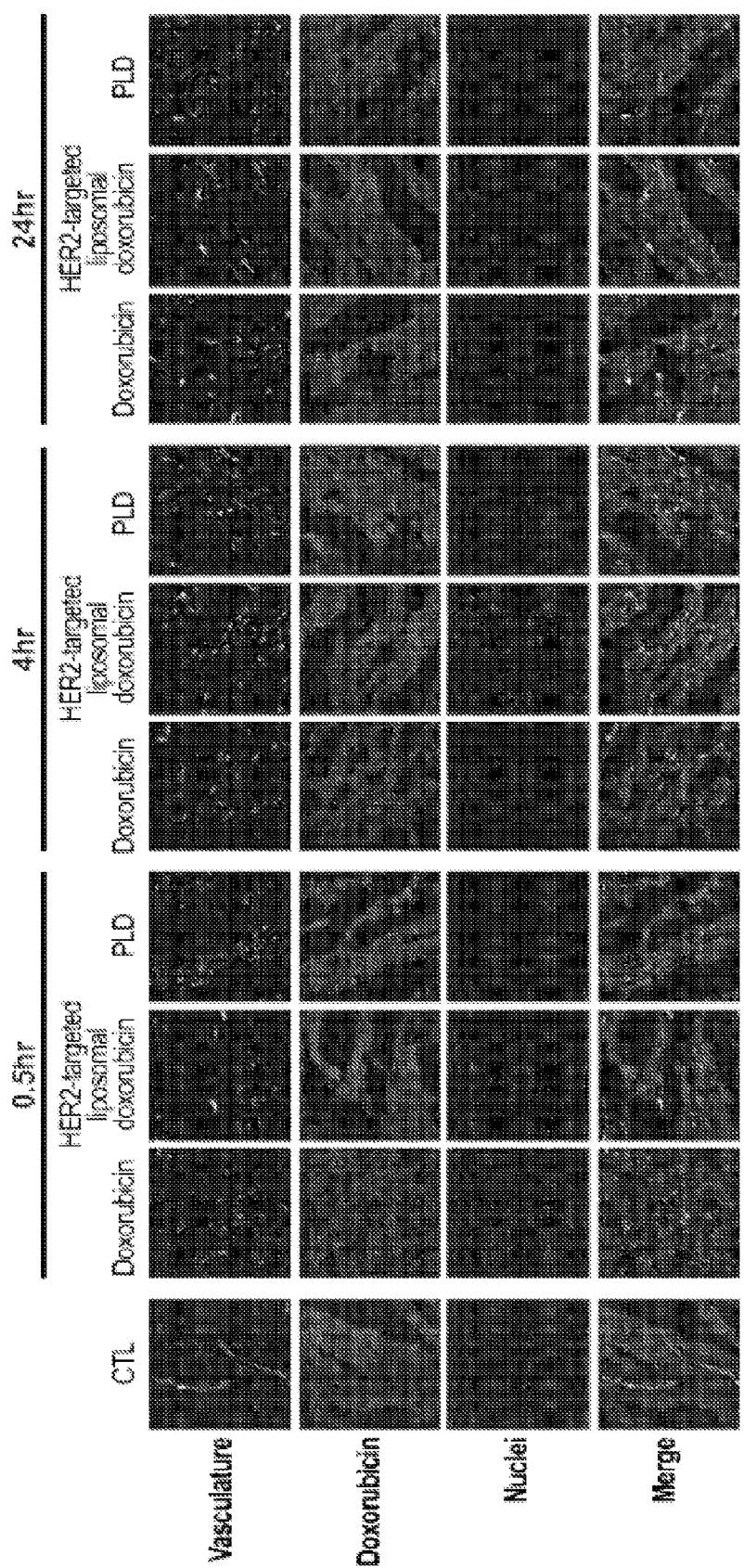
FIG. 7D represents confocal fluorescence microscopy photomicrographs illustrating the biodistribution and accumulation of doxorubicin in heart tissue over time in Nu/nu mice injected intravenously with MM-302-DiI5, PLD-DiI5, and free doxorubicin at 3 mg/kg (dox equiv.).
Figure 7E:
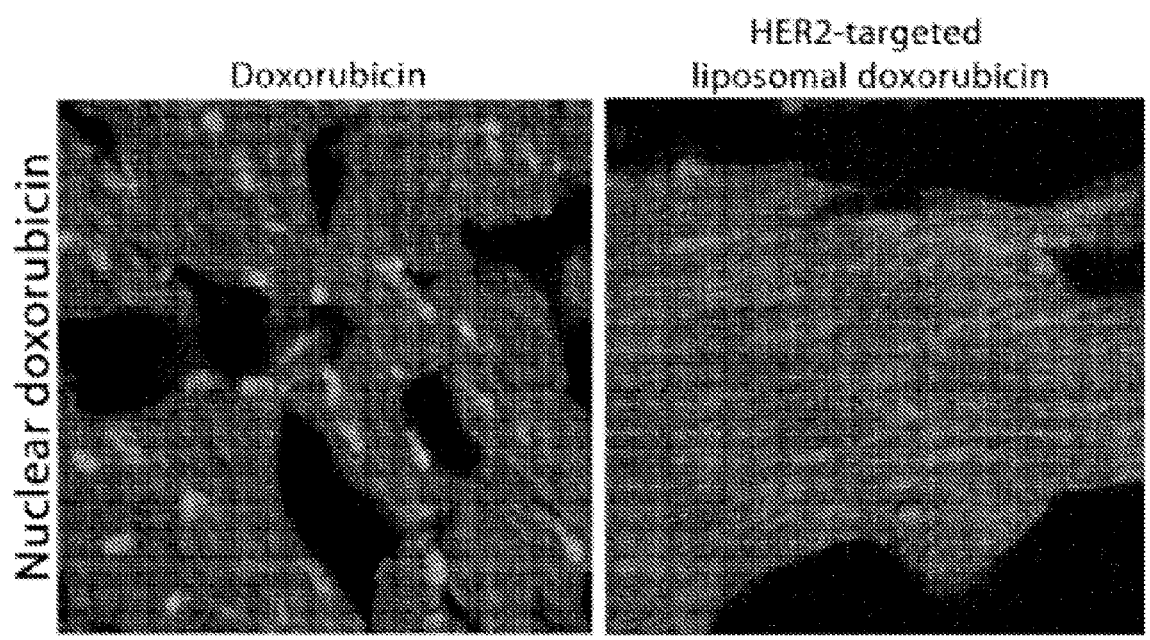
FIG. 7E depicts a higher magnification (2×) of the confocal fluorescence microscopy photomicrograph illustrating the overlay of the nuclei and doxorubicin signal images as shown in FIG. 7D for the 0.5 h time points for doxorubicin and MM-302.

MM-302 Results in Lower Nuclear Doxorubicin Accumulation in Mouse Tissue Compared to Free Doxorubicin The microdistribution of doxorubicin (naturally fluorescent) and liposomes (DiI5-labelled) was analyzed in cryosections generated from heart tissues of mice injected with either free doxorubicin, MM-302-DiI5 or PLD-DiI5 (all at 3 mg/kg dox equiv) at 0.5, 4 and 24 h post injection. In order to visualize the heart vasculature, mice were injected i.v. with FITC-lectin 5 min before sacrificing. Heart slices were imaged by fluorescence confocal microscopy. Representative fields for the different treatment groups at the three time points analyzed (0.5, 4 and 24 h) are shown in FIG. 7D. Untreated hearts were also imaged and a representative image is shown in FIG. 7D (left panels). Co-localization of doxorubicin with the nuclear signal is shown in the bottom panels of FIG. 7D. Higher magnification images of the nuclear doxorubicin signal are shown in FIG. 7E, for both doxorubicin and MM-302 at the 0.5 h time point. While with MM-302 no doxorubicin signal is visible in the nuclei, with free doxorubicin the majority of the nuclei are doxorubicin-positive. The images were analyzed as described above and the percent of doxorubicin-positive nuclei determined. Injection of free doxorubicin resulted in a prominent nuclear accumulation of doxorubicin at 0.5 h, with about 50% of the nuclei positive for doxorubicin. By 4 h, however, only 23% of the nuclei were positive for doxorubicin and the signal returned to basal levels at 24 h.

Figure 7F:
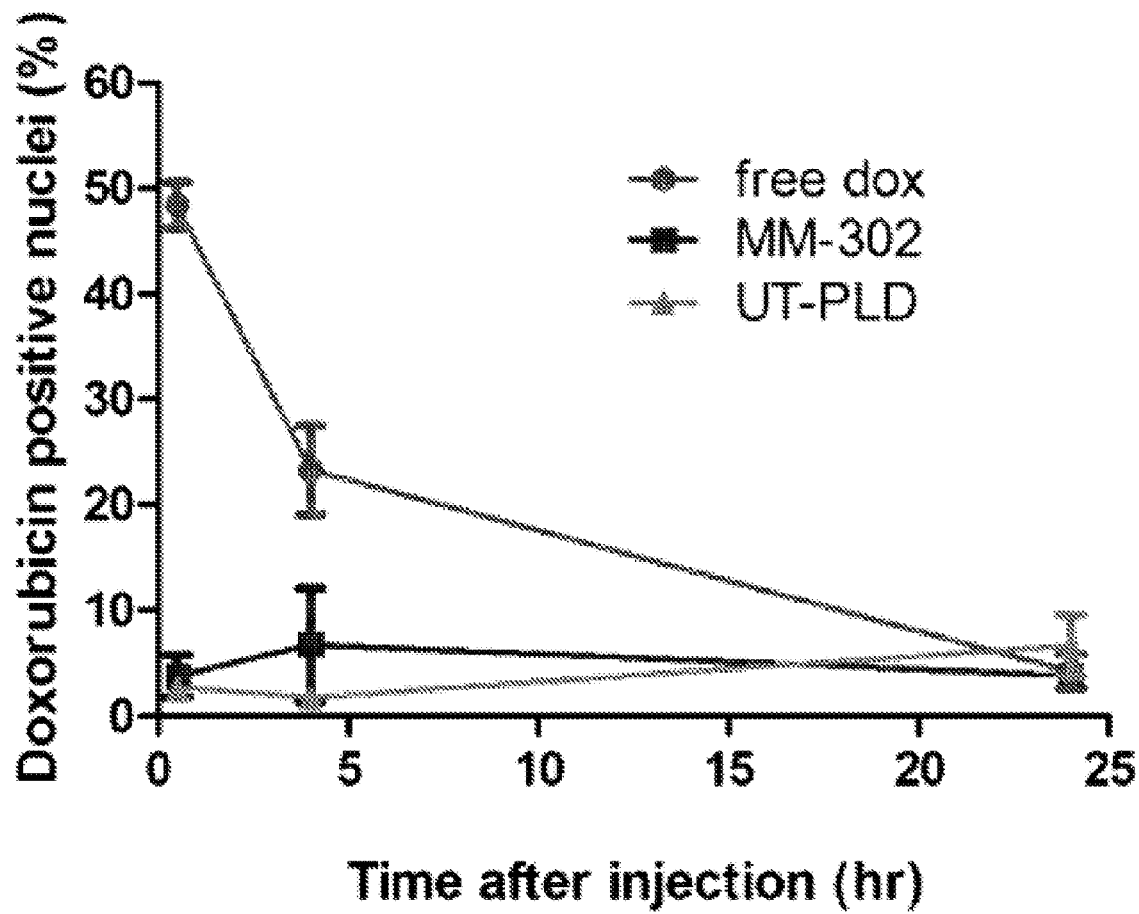
FIG. 7F depicts a line graph illustrating the percentage of doxorubicin positive nuclei in heart tissue of Nu/nu mice injected intravenously with MM-302-DiI5, PLD-DiI5, and free doxorubicin at 3 mg/kg (dox equiv.) quantified using Definiens® Developer XD™.

With the liposomal formulations, little to no signal was detected for the majority of fields of view. Occasional signal in the DiI5 channel (liposome) was detected. In these cases, the liposome signal predominantly co-localized with the FITC-lectin signal, indicating liposomes that had not extravasated into the heart tissue but still remained in the vascular compartment. Upon MM-302-DiI5 or PLD-DiI5 treatment, doxorubicin was not detected in the nucleus in the majority of the heart fields analyzed, independent of time point. In one of the four MM-302-DiI5 hearts collected at 0.5 h and in one of the four MM-302-DiI5 hearts collected at 4 h, a liposomal signal was detected in the extravascular space and doxorubicin was found in a small percentage of the nuclei. Similarly, in one of four PLD hearts collected at 0.5 h and in two of four PLD heart collected at 24 h, images revealed the extravascular liposomal signal and presence of nuclear doxorubicin. These fields are not presented as representative images, however their values were considered for the quantification shown in FIG. 7F. The area under the curves of both MM-302 and PLD were statistically significantly lower than the free doxorubicin AUC (p<0.001). No significant differences were observed between the AUCs of MM-302 and PLD.

In order to get a broader visualization of the distribution of doxorubicin and of the liposomes in the heart tissue, full heart section scans were taken. The full section heart scans visually confirmed the results of the confocal microscopy, showing a broad doxorubicin distribution with nuclear localization upon free doxorubicin injection, and only rare liposome and doxorubicin signals in the hearts of mice injected with either DiI5 MM-302 or DiI5 PLD.

In summary, treatment with either MM-302 or PLD showed significantly lower nuclear doxorubicin accumulation than was seen following treatment with free doxorubicin, while this did not differ significantly between MM-302 and PLD.

Equivalents

Those skilled in the art will recognize, or be able to ascertain and implement using no more than routine experimentation, many equivalents of the specific embodiments described herein. Such equivalents are intended to be encompassed by the following claims. Any combinations of the embodiments disclosed in the dependent claims are contemplated to be within the scope of the disclosure.

INCORPORATION BY REFERENCE

The disclosure of each and every U.S. and foreign patent and pending patent application and publication referred to herein is specifically incorporated by reference herein in its entirety.

What is claimed is:

1. A method of treating a human patient with locally advanced/unresectable or metastatic advanced breast cancer that overexpresses ErbB2 (HER2) receptors, the method comprising administering to the human patient 30 mg/m$^2$ of doxorubicin (doxorubicin HCl equivalent) in a MM302 doxorubicin HER-2 targeted immunoliposome once every three weeks to treat the breast cancer that overexpresses HER2.

2. The method of claim 1, wherein the breast cancer characterized by overexpression of HER2 receptor is further characterized as being HER2 FISH positive.

3. The method of claim 1, wherein the breast cancer characterized by overexpression of ErbB2 receptor further characterized as expressing an average of at least 200,000 cell surface ErbB2 receptors per cell.

4. The method of claim 1, wherein the cumulative concentration of doxorubicin administered to the patient in the MM302 doxorubicin HER-2 targeted immunoliposome is less than 550 mg/m$^2$.

5. The method of claim 1, wherein the patient is anthracycline-naïve prior to treatment with the MM302 doxorubicin HER-2 targeted immunoliposome.

6. The method of claim 1, wherein the MM302 doxorubicin HER-2 targeted immunoliposome is administered intravenously over 60 minutes.

7. The method of claim 1, comprising treating the patient for breast cancer that is characterized by expression of HER2 receptor characterized as being HER2$^{3+}$ or HER2$^{2+}$ and HER2 FISH positive.

8. The method of claim 7, wherein the patient is anthracycline-naive prior to treatment with the MM302 doxorubicin HER-2 targeted immunoliposome.

9. The method of claim 1, wherein the breast cancer is HER2$^{3+}$.

10. The method of claim 1, wherein the breast cancer is FISH positive.

11. The method of claim 1, wherein the breast cancer is HER2$^{2+}$ and is FISH positive.

12. The method of claim 1, wherein the breast cancer is HER2$^{3+}$ and is FISH positive.

13. The method of claim 1, wherein the cumulative concentration of doxorubicin administered to the patient in the MM-302 doxorubicin HER2 targeted immunoliposome is less than 550 mg/m$^2$.

14. The method of claim 1, wherein the breast cancer is HER2$^{3+}$ and the patient is anthracycline naïve.

15. The method of claim 1, wherein the breast cancer is HER2$^{2+}$ and HER2 FISH positive and the patient is anthracycline naïve.

16. The method of claim 14, wherein the cumulative concentration of doxorubicin administered to the patient in the MM302 doxorubicin HER2 targeted immunoliposome is less than 550 mg/m$^2$.

17. A method of treating a human patient with locally advanced/unresectable or metastatic advanced breast cancer that is HER2 FISH positive and HER2$^{2+}$ or is HER2$^{3+}$, the method comprising administering to the human patient 30 mg/m$^2$ of doxorubicin (HCl equivalent) in a MM302 doxorubicin HER-2 targeted immunoliposome once every three weeks to treat the breast cancer, wherein the human patient is anthracycline-naïve prior to treatment with the MM302 doxorubicin HER-2 targeted immunoliposome.

18. The method of claim 17, wherein the breast cancer is HER2$^{2+}$ and FISH positive.

19. The method of claim 17, wherein the breast cancer is HER2$^{3+}$.

20. A method of treating a human patient with breast cancer that is HER2 FISH positive and HER2$^{2+}$ or is HER2$^{3+}$, the method comprising administering to the human patient 30 mg/m$^2$ of doxorubicin (doxorubicin HCl equivalent) in a MM302 doxorubicin HER-2 targeted immunoliposome once every three weeks to treat the breast cancer.

21. The method of claim 20, wherein the breast cancer is FISH positive.

22. The method of claim 20, wherein the human patient is anthracycline-naïve prior to treatment with the MM302 doxorubicin HER-2 targeted immunoliposome and the cumulative concentration of doxorubicin administered to the human patient is less than 550 mg/m$^2$.

* * * * *